(12) United States Patent
Gabibov et al.

(10) Patent No.: US 7,560,529 B2
(45) Date of Patent: Jul. 14, 2009

(54) METHOD FOR PRODUCING CATALYTIC ANTIBODIES (VARIANTS), ANTIGENS FOR IMMUNIZATION AND NUCLEOTIDE SEQUENCE

(75) Inventors: Alexandr Gabibovich Gabibov, Moscow (RU); Natalya Alexandrovna Ponomarenko, Moscow (RU); Alexandr Vladimirovich Kolesnikov, Moscow (RU); Ivan Ivanovich Vorobiev, Moscow (RU); Elena Sergeevna Alexandrova, Moscow (RU); Alexandr Viktorovich Demin, Moskovskaya Oblast (RU)

(73) Assignee: FDS Pharma, Esher, Surrey (GB)

( * ) Notice: Subject to any disclaimer, the term of this patent is extended or adjusted under 35 U.S.C. 154(b) by 0 days.

(21) Appl. No.: 11/644,907

(22) Filed: Dec. 26, 2006

(65) Prior Publication Data
US 2007/0178109 A1   Aug. 2, 2007

Related U.S. Application Data

(63) Continuation-in-part of application No. 10/475,706, filed as application No. PCT/RU02/00177 on Apr. 18, 2002, now abandoned.

(30) Foreign Application Priority Data
Apr. 24, 2001   (RU) .............................. 2001110759

(51) Int. Cl.
C07K 14/00   (2006.01)
(52) U.S. Cl. ...................................... 530/350
(58) Field of Classification Search ........................ None
See application file for complete search history.

(56) References Cited

U.S. PATENT DOCUMENTS

| 5,817,629 A | 10/1998 | Warren et al. |
| 5,948,764 A | 9/1999 | Gaur et al. |
| 5,961,973 A | 10/1999 | Crea |
| 6,140,091 A | 10/2000 | Raso et al. |

FOREIGN PATENT DOCUMENTS

| RU | 94045907 | 11/1996 |
| WO | WO 97/03696 | 2/1997 |

OTHER PUBLICATIONS

Ponomarenko et al., "Induction of a Protein-Targeted Catalytic Response in Autoimmune Prone Mice: Antibody-Mediated Cleavage of HIV-1 Glycoprotein GP120", Biochemistry, 2006, vol. 45, No. 1, pp. 324-330.
Gabibov et al., "Antibody Proteases: Induction of Catalytic Response", Biochemistry, vol. 67, No. 10, 2002, pp. 1167-1179.
Ronomarenko et al., "Catalytic antibodies in clinical and experimental pathology: human and mouse models", Journal of Immunological Methods, vol. 269, 2002, pp. 197-211.
Ponomarenko, N.A., et al. (2002) J. Immun. Meth. 269, 1970211.
Vilcaes, A.A., et al. (2005) J. neuroimmun. 164, 31-36.

*Primary Examiner*—Nashaat T Nashed
*Assistant Examiner*—Md. Younus Meah
(74) *Attorney, Agent, or Firm*—Young & Thompson

(57) ABSTRACT

A method for producing catalytic antibodies to proteins and peptides, in particular to gp120, using animals having spontaneous and induced autoimmune pathologies. The method makes it possible to create a catalytic vaccine which can when injected to a patient to exhibits adhesive properties in relation to antigen simultaneously with a destructive function, thereby suspending the progression of disease. The method for the autoimmunisation of animal lines SJL by fused proteins containing classical peptide epitope which develops pathology of an animal by protein fragments gp120 accompanied with an interest target catalytic antibody is disclosed. Also the method for immunising autoimmune animals by highly reactive chemical compositions which can perform a covalent selection of catalytic clones containing peptide fragments of potential resected portions gp120 is disclosed.

6 Claims, 21 Drawing Sheets

Figure 2:
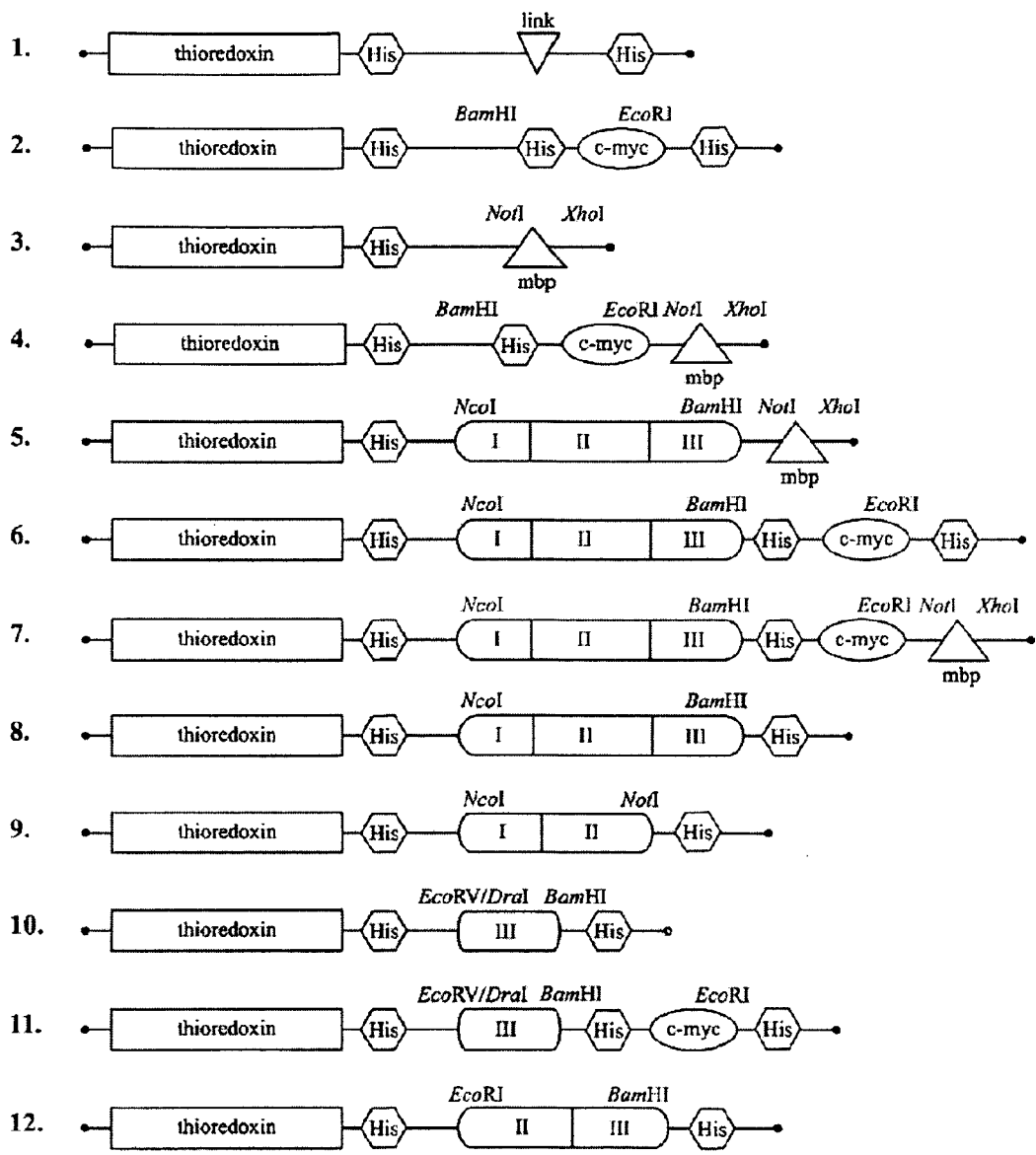

```
ccatggctacagaaaaattgtgggtcacagtctattatggggtacctgtgtggaaggaagcaac
caccactctatttgtgcatcagatgctaaagcatatgatacagaggtacataatgtttgggcc
acacatgcctgtgtacccacagaccccaacccacaagaagtagtattgagctgcaacacctctg
tcattacacaggcctgtccaaaggtatcctttgagccaattcccatacattattgtgccccggc
tggttttgcgattctaaaatgtaataataagacgttcaatggaacaggaccatgtacaaatgtc
agcacagtacaatgtacacatggaattaggccagtagtatcaactcaactgctgttaaatggca
gtctagcagaagaagaggtagtaattagatctgtcaatttcacggacaatgctaaaaccataat
agtacagctgaacacatctgtagaaattaattgtacacattgtaacattagtagagcaaaatgg
aataacactttaaaacagatagctagcaaattaagagaacaatttggaaataataaaacaataa
tctttaagcaatcctcaggaggggacccagaaattgtaacgcacagttttaattgtggaggggga
atttttctactgtaattcaacacaactgtttaatagtacttggtttaatagtacttggagtact
gaagggtcaaataacactgaaggaagtgacacaatcaccctcccatgcagaataaaacaaatta
taaacatgtggcagaaagtaggaaaagcaatgtatgcccctcccatcagtggacaaattagatg
ttcatcaaatattacagggctgctattaacaagagatggtggtaatagcaacaatgagtccgag
atcttcagacctggaggaggagatatgagggacaattggagaagtgaattatataaatataaag
tagtaaaaattgaaccattaggagtagcacccaccaaggcaaagtgataactggatcct
```

FIG. 1A-1

MATEKLWVTVYYGVPVWKEATTTLFCASDAKAYDTEVHNVWATHACVPTDPNPQEVVLSCNTSV
ITQACPKVSFEPIPIHYCAPAGFAILKCNNKTFNGTGPCTNVSTVQCTHGIRPVVSTQLLLNGS
LAEEEVVIRSVNFTDNAKTIIVQLNTSVEINCTHCNISRAKWNNTLKQIASKLREQFGNNKTII
FKQSSGGDPEIVTHSFNCGGEFFYCNSTQLFNSTWFNSTWSTEGSNNTEGSDTITLPCRIKQII
NMWQKVGKAMYAPPISGQIRCSSNITGLLLTRDGGNSNNESEIFRPGGGDMRDNWRSELYKYKV
VKIEPLGVAPTKAK

FIG. 1A-2

```
ccatggctacagaaaaattgtgggtcacagtctattatggggtacctgtgtggaaggaagcaac
caccactctatttgtgcatcagatgctaaagcatatgatacagaggtacataatgtttgggcc
acacatgcctgtgtacccacagaccccaacccacaagaagtagtattgagctgcaacacctctg
tcattacacaggcctgtccaaaggtatcctttgagccaattcccatacattattgtgccccggc
tggttttgcgattctaaaatgtaataataagacgttcaatggaacaggaccatgtacaaatgtc
agcacagtacaatgtacacatggaattaggccagtagtatcaactcaactgctgttaaatggca
gtctagcagaagaagaggtagtaattagatctgtcaatttcacggacaatgctaaaaccataat
agtacagctgaacacatctgtagaaattaattgtacacattgtaacattagtagagcaaaatgg
aataacactttaaaacagatagctagcaaattaagagaacaatttggaaataataaaacaataa
tctttaagcaatcctcaggagggggacccagaaattgtaacgcacagttttaattgtggaggggga
attttctactgtaattcaacacaactgtttaatagtacttggtttaatagtacttggagtact
gaagggtcaaataacactgaaggaagtgacacaatcaccctcccatgcagaataaaacaaatta
taaacatgtggcagaaagtaggaaaagcaatgtatgcccctcccatcagtggacaaattagatg
ttcatcaaatattacagggctgctattaacaagagatggtggtaatagcaacaatgagtccgag
atcttcagacctggaggaggagatatgagggacaattggagaagtgaattatataaatataaag
tagtaaaaattgaaccattaggagtagcacccaccaaggcaaagctggatccgaattcgagctc
cgtcgacaagcttgcggccgcactcgagcaccaccaccaccaccactga
```

FIG. 1B-1

MATEKLWVTVYYGVPVWKEATTTLFCASDAKAYDTEVHNVWATHACVPTDPNPQEVVLSCNTSV
ITQACPKVSFEPIPIHYCAPAGFAILKCNNKTFNGTGPCTNVSTVQCTHGIRPVVSTQLLLNGS
LAEEEVVIRSVNFTDNAKTIIVQLNTSVEINCTHCNISRAKWNNTLKQIASKLREQFGNNKTII
FKQSSGGDPEIVTHSFNCGGEFFYCNSTQLFNSTWFNSTWSTEGSNNTEGSDTITLPCRIKQII
NMWQKVGKAMYAPPISGQIRCSSNITGLLLTRDGGNSNNESEIFRPGGGDMRDNWRSELYKYKV
VKIEPLGVAPTKAKLDPNSSSVDKLAAALEHHHHHH

FIG. 1B-2

```
ccatggctacagaaaaattgtgggtcacagtctattatggggtacctgtgtggaaggaagcaac
caccactctatttgtgcatcagatgctaaagcatatgatacagaggtacataatgtttgggcc
acacatgcctgtgtacccacagaccccaacccacaagaagtagtattgagctgcaacacctctg
tcattacacaggcctgtccaaaggtatcctttgagccaattcccatacattattgtgccccggc
tggttttgcgattctaaaatgtaataataagacgttcaatggaacaggaccatgtacaaatgtc
agcacagtacaatgtacacatggaattaggccagtagtatcaactcaactgctgttaaatggca
gtctagcagaagaagaggtagtaattagatctgtcaatttcacggacaatgctaaaaccataat
agtacagctgaacacatctgtagaaattaattgtacacattgtaacattagtagagcaaaatgg
aataacactttaaaacagatagctagcaaattaagagaacaatttggaaataataaaacaataa
tctttaagcaatcctcaggagggggacccagaaattgtaacgcacagttttaattgtggaggga
attttctactgtaattcaacacaactgtttaatagtacttggtttaatagtacttggagtact
gaagggtcaaataacactgaaggaagtgacacaatcaccctcccatgcagaataaaacaaatta
taaacatgtggcagaaagtaggaaaagcaatgtatgcccctcccatcagtggacaaattagatg
ttcatcaaatattacagggctgctattaacaagagatggtggtaatagcaacaatgagtccgag
atcttcagacctggaggaggagatatgagggacaattggagaagtgaattatataaatataaag
tagtaaaaattgaaccattaggagtagcacccaccaaggcaaagctggatccgaattcgagctc
cgtcgacaagcttgcggccgcagtagtccatttcttcaagaacattgtgacacctcgaacacca
cctccatcctaactcgag
```

FIG. 1C-1

```
MATEKLWVTVYYGVPVWKEATTTLFCASDAKAYDTEVHNVWATHACVPTDPNPQEVVLSCNTSV
ITQACPKVSFEPIPIHYCAPAGFAILKCNNKTFNGTGPCTNVSTVQCTHGIRPVVSTQLLLNGS
LAEEEVVIRSVNFTDNAKTIIVQLNTSVEINCTHCNISRAKWNNTLKQIASKLREQFGNNKTII
FKQSSGGDPEIVTHSFNCGGEFFYCNSTQLFNSTWFNSTWSTEGSNNTEGSDTITLPCRIKQII
NMWQKVGKAMYAPPISGQIRCSSNITGLLLTRDGGNSNNESEIFRPGGGDMRDNWRSELYKYKV
VKIEPLGVAPTKAKLDPNSSSVDKLAAAVVHFFKNIVTPRTPPPS
```

FIG. 1C-2

```
ccatggctacagaaaaattgtgggtcacagtctattatggggtacctgtgtggaaggaagcaac
caccactctatttgtgcatcagatgctaaagcatatgatacagaggtacataatgtttgggcc
acacatgcctgtgtacccacagaccccaacccacaagaagtagtattgagctgcaacacctctg
tcattacacaggcctgtccaaaggtatcctttgagccaattcccatacattattgtgccccggc
tggttttgcgattctaaaatgtaataataagacgttcaatggaacaggaccatgtacaaatgtc
agcacagtacaatgtacacatggaattaggccagtagtatcaactcaactgctgttaaatggca
gtctagcagaagaaggtagtaattagatctgtcaatttcacggacaatgctaaaaccataat
agtacagctgaacacatctgtagaaattaattgtacacattgtaacattagtagagcaaaatgg
aataacactttaaaacagatagctagcaaattaagagaacaatttggaaataataaaacaataa
tctttaagcaatcctcaggaggggacccagaaattgtaacgcacagttttaattgtggaggga
atttttctactgtaattcaacacaactgtttaatagtacttggtttaatagtacttggagtact
gaagggtcaaataacactgaaggaagtgacacaatcaccctcccatgcagaataaaacaaatta
taaacatgtggcagaaagtaggaaaagcaatgtatgcccctcccatcagtggacaaattagatg
ttcatcaaatattacagggctgctattaacaagagatggtggtaatagcaacaatgagtccgag
atcttcagacctggaggaggagatatgagggacaattggagaagtgaattatataaatataaag
tagtaaaaattgaaccattaggagtagcacccaccaaggcaaagctggatccgcaccaccacca
ccaccacggttccggtgaacaaaaactcatctcagaagaggatctgaattcgagctccgtcgac
aagcttgcggccgcagtagtccatttcttcaagaacattgtgacacctcgaacaccacctccat
cctaactcgag
```

FIG. 1D-1

```
MATEKLWVTVYYGVPVWKEATTTLFCASDAKAYDTEVHNVWATHACVPTDPNPQEVVLSCNTSV
ITQACPKVSFEPIPIHYCAPAGFAILKCNNKTFNGTGPCTNVSTVQCTHGIRPVVSTQLLLNGS
LAEEEVVIRSVNFTDNAKTIIVQLNTSVEINCTHCNISRAKWNNTLKQIASKLREQFGNNKTII
FKQSSGGDPEIVTHSFNCGGEFFYCNSTQLFNSTWFNSTWSTEGSNNTEGSDTITLPCRIKQII
NMWQKVGKAMYAPPISGQIRCSSNITGLLLTRDGGNSNNESEIFRPGGGDMRDNWRSELYKYKV
VKIEPLGVAPTKAKLDPHHHHHHGSGEQKLISEEDLNSSSVDKLAAAVVHFFKNIVTPRTPPPS
```

FIG. 1D-2

Constructs based on pET28a plasmid
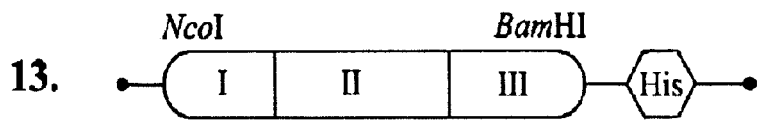
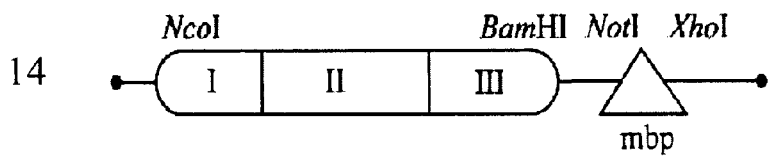
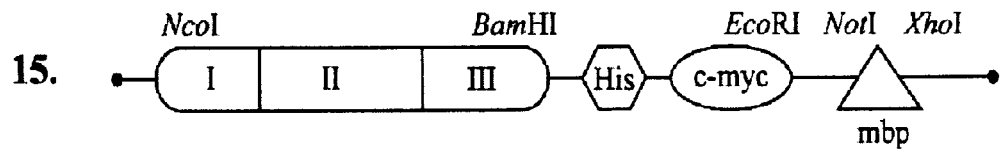
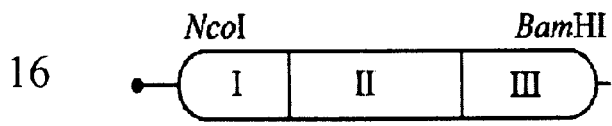
Nucleotide sequences coding:
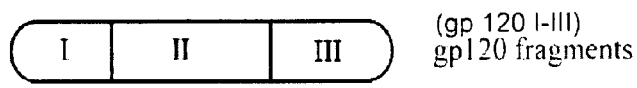
(gp 120 I-III)
gp120 fragments
△ mbp
VVHFFKNIVTPRTPPPS
MBP peptide 89-104
⬡ His   hexahistidine tag
⬯ c-myc   EQKLISEEDL
epitope from p62-myc protein
The restriction sites for the restrictases are indicated in italics.
FIG. 3

A
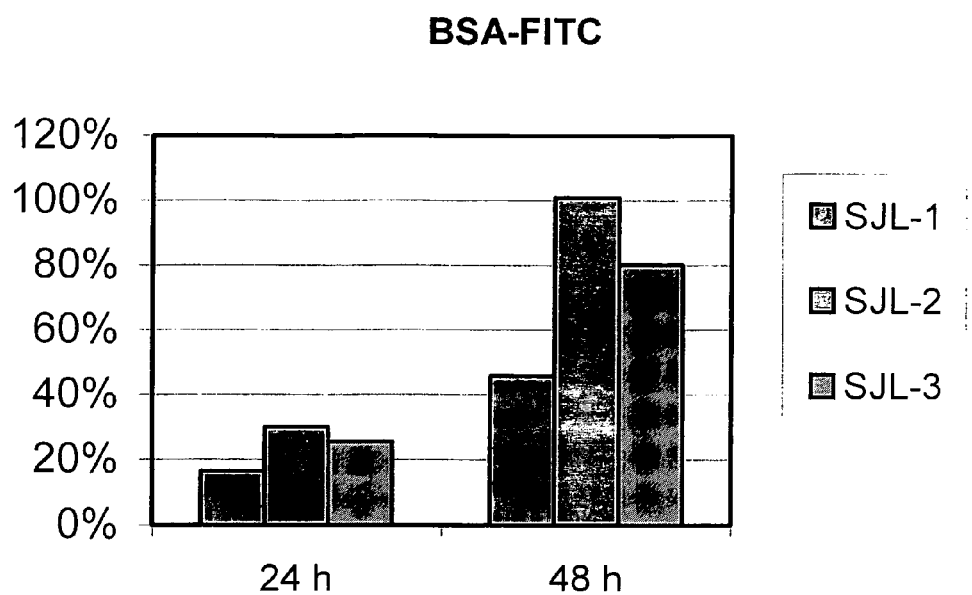
B
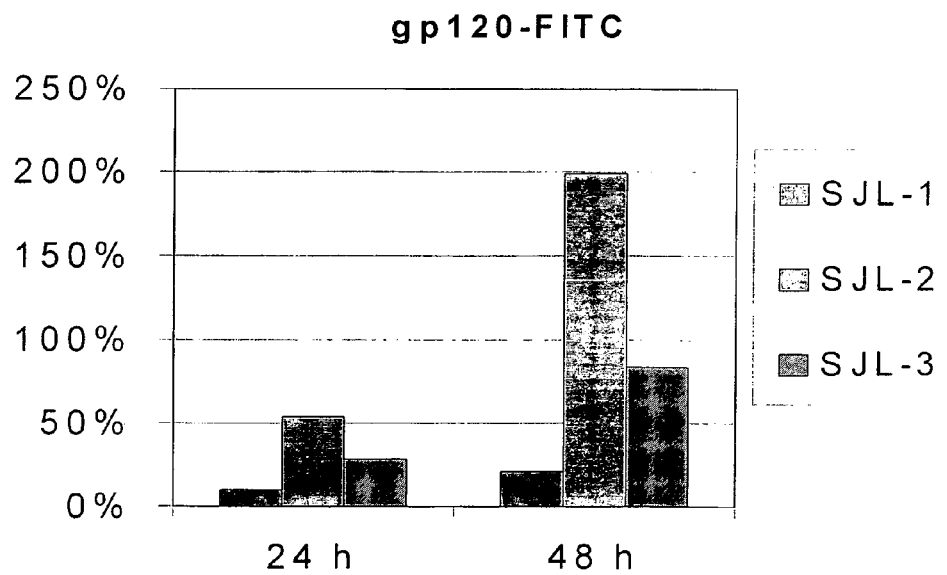
FIG. 7

Immunogenic Potential of Chimerical Proteins containing fragment gp120 I-III,
in autoimmune (SJL) and normal (conventional BALB/c) mice.

Table 1. Specific Immune Response of SJL and BALB/c Mice measured by ELISA.

| Mice | Immunogen, the product of Construct No** | Dose | Antigens | | | | Rec. protein gp120 | $MBP_{89-104}$ |
|---|---|---|---|---|---|---|---|---|
| | | | The product of Construct No. * | | | | | |
| | | | 8 | 9 | 10 | 3 | | |
| | | Mcg/mouse | | | | | | |
| SJL | Control | - | - | - | - | - | - | - |
| SJL | 16 | 150 | + | + | + | - | + | - |
| SJL | 16 | 300 | + | + | + | - | + | - |
| SJL | 13 | 150 | + | + | + | - | + | - |
| SJL | 13 | 300 | + | + | + | - | + | - |
| SJL | 15 | 150 | + | + | + | + | + | + |
| SJL | 15 | 300 | + | + | + | + | + | + |
| SJL | 14 | 150 | + | + | + | + | + | - |
| SJL | 14 | 300 | + | + | + | + | + | - |
| BALB/c | Control | - | - | - | - | - | - | - |
| BALB/c | 16 | 150 | + | + | + | - | + | - |
| BALB/c | 16 | 300 | + | + | + | - | + | - |
| BALB/c | 13 | 150 | + | + | + | - | + | - |
| BALB/c | 13 | 300 | + | + | + | - | + | - |
| BALB/c | 15 | 150 | + | + | + | + | + | + |
| BALB/c | 15 | 300 | + | + | + | + | + | + |
| BALB/c | 14 | 150 | + | + | + | + | + | + |
| BALB/c | 14 | 300 | + | + | + | + | + | + |

NOTE: * SEE FIG 2
\*\*SEE FIG.3

FIG.14

```
                         SEQUENCE LISTING

<160> NUMBER OF SEQ ID NOS: 25

<210> SEQ ID NO 1
<211> LENGTH: 332
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Thr Glu Lys Leu Trp Val Thr Val Tyr Tyr Gly Val Pro Val Trp Lys
 1               5                  10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Ser Cys Asn Thr Ser Val Ile Thr
    50                  55                  60

Gln Ala Cys Pro Lys Val Ser Phe Glu Pro Ile Pro Ile His Tyr Cys
65                  70                  75                  80

Ala Pro Ala Gly Phe Ala Ile Leu Lys Cys Asn Asn Lys Thr Phe Asn
                85                  90                  95

Gly Thr Gly Pro Cys Thr Asn Val Ser Thr Val Gln Cys Thr His Gly
            100                 105                 110

Ile Arg Pro Val Val Ser Thr Gln Leu Leu Leu Asn Gly Ser Leu Ala
        115                 120                 125

Glu Glu Glu Val Val Ile Arg Ser Val Asn Phe Thr Asp Asn Ala Lys
    130                 135                 140

Thr Ile Ile Val Gln Leu Asn Thr Ser Val Glu Ile Asn Cys Thr His
145                 150                 155                 160

Cys Asn Ile Ser Arg Ala Lys Trp Asn Asn Thr Leu Lys Gln Ile Ala
                165                 170                 175

Ser Lys Leu Arg Glu Gln Phe Gly Asn Asn Lys Thr Ile Ile Phe Lys
            180                 185                 190

Gln Ser Ser Gly Gly Asp Pro Glu Ile Val Thr His Ser Phe Asn Cys
        195                 200                 205

Gly Gly Glu Phe Phe Tyr Cys Asn Ser Thr Gln Leu Phe Asn Ser Thr
    210                 215                 220

Trp Phe Asn Ser Thr Trp Ser Thr Glu Gly Ser Asn Asn Thr Glu Gly
225                 230                 235                 240

Ser Asp Thr Ile Thr Leu Pro Cys Arg Ile Lys Gln Ile Ile Asn Met
                245                 250                 255
```

```
Trp Gln Lys Val Gly Lys Ala Met Tyr Ala Pro Pro Ile Ser Gly Gln
            260                 265                 270

Ile Arg Cys Ser Ser Asn Ile Thr Gly Leu Leu Thr Arg Asp Gly
        275                 280                 285

Gly Asn Ser Asn Asn Glu Ser Glu Ile Phe Arg Pro Gly Gly Asp
    290                 295                 300

Met Arg Asp Asn Trp Arg Ser Glu Leu Tyr Lys Tyr Lys Val Val Lys
305                 310                 315                 320

Ile Glu Pro Leu Gly Val Ala Pro Thr Lys Ala Lys
                325                 330
```

<210> SEQ ID NO 2
<211> LENGTH: 18
<212> TYPE: PRT
<213> ORGANISM: Bacteriophage f1

<400> SEQUENCE: 2

```
Met Lys Lys Leu Leu Phe Ala Ile Pro Leu Val Val Pro Phe Tyr Ser
  1               5                  10                  15

His Ser
```

<210> SEQ ID NO 3
<211> LENGTH: 19
<212> TYPE: PRT
<213> ORGANISM: Mus musculus

<400> SEQUENCE: 3

```
Met Asn Phe Gly Leu Arg Leu Ile Phe Leu Val Leu Thr Leu Lys Gly
  1               5                  10                  15

Val Gln Cys
```

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Leu Asp Pro Asn Ser Ser Ser Val Asp Lys Leu Ala Ala Ala Leu Glu
  1               5                  10                  15

His His His His His His
            20
```

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Leu Asp Pro Asn Ser Ser Ser Val Asp Lys Leu Ala Ala Ala Val Val
  1               5                  10                  15

His Phe Phe Lys Asn Ile Val Thr Pro Arg Thr Pro Pro Pro Ser
            20                  25                  30
```

<210> SEQ ID NO 6
<211> LENGTH: 17
<212> TYPE: PRT

```
<213> ORGANISM: Mus musculus

<400> SEQUENCE: 6

Val Val His Phe Phe Lys Asn Ile Val Thr Pro Arg Thr Pro Pro Pro
 1               5                  10                  15

Ser

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Asp Pro His His His His His His
 1               5

<210> SEQ ID NO 8
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gly Glu Gln Lys Leu Ile Ser Glu Glu Asp Leu Asn Ser Ser
 1               5                  10                  15

Ser Val Asp Lys Leu Ala Ala Ala Val Val His Phe Phe Lys Asn Ile
                20                  25                  30

Val Thr Pro Arg Thr Pro Pro Ser
                35                  40

<210> SEQ ID NO 9
<211> LENGTH: 10
<212> TYPE: PRT
<213> ORGANISM: Homo sapiens

<400> SEQUENCE: 9

Glu Gln Lys Leu Ile Ser Glu Glu Asp Leu
 1               5                  10

<210> SEQ ID NO 10
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Asp Pro His His His His His His Gly Ser Gly Glu Gln Lys Leu
 1               5                  10                  15

Ile Ser Glu Glu Asp Leu Asn Ser Ser Ser Val Asp Lys Leu Ala Ala
                20                  25                  30

Ala Val Val His Phe Phe Lys Asn Ile Val Thr Pro Arg Thr Pro Pro
                35                  40                  45

Pro Ser
     50

<210> SEQ ID NO 11
```

```
<211> LENGTH: 334
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Met Ala Thr Glu Lys Leu Trp Val Thr Val Tyr Tyr Gly Val Pro Val
 1               5                  10                  15

Trp Lys Glu Ala Thr Thr Thr Leu Phe Cys Ala Ser Asp Ala Lys Ala
             20                  25                  30

Tyr Asp Thr Glu Val His Asn Val Trp Ala Thr His Ala Cys Val Pro
         35                  40                  45

Thr Asp Pro Asn Pro Gln Glu Val Val Leu Ser Cys Asn Thr Ser Val
     50                  55                  60

Ile Thr Gln Ala Cys Pro Lys Val Ser Phe Glu Pro Ile Pro Ile His
 65                  70                  75                  80

Tyr Cys Ala Pro Ala Gly Phe Ala Ile Leu Lys Cys Asn Asn Lys Thr
                 85                  90                  95

Phe Asn Gly Thr Gly Pro Cys Thr Asn Val Ser Thr Val Gln Cys Thr
            100                 105                 110

His Gly Ile Arg Pro Val Val Ser Thr Gln Leu Leu Leu Asn Gly Ser
        115                 120                 125

Leu Ala Glu Glu Glu Val Val Ile Arg Ser Val Asn Phe Thr Asp Asn
    130                 135                 140

Ala Lys Thr Ile Ile Val Gln Leu Asn Thr Ser Val Glu Ile Asn Cys
145                 150                 155                 160

Thr His Cys Asn Ile Ser Arg Ala Lys Trp Asn Asn Thr Leu Lys Gln
                165                 170                 175

Ile Ala Ser Lys Leu Arg Glu Gln Phe Gly Asn Asn Lys Thr Ile Ile
            180                 185                 190

Phe Lys Gln Ser Ser Gly Gly Asp Pro Glu Ile Val Thr His Ser Phe
        195                 200                 205

Asn Cys Gly Gly Glu Phe Phe Tyr Cys Asn Ser Thr Gln Leu Phe Asn
    210                 215                 220

Ser Thr Trp Phe Asn Ser Thr Trp Ser Thr Glu Gly Ser Asn Asn Thr
225                 230                 235                 240

Glu Gly Ser Asp Thr Ile Thr Leu Pro Cys Arg Ile Lys Gln Ile Ile
                245                 250                 255

Asn Met Trp Gln Lys Val Gly Lys Ala Met Tyr Ala Pro Pro Ile Ser
            260                 265                 270

Gly Gln Ile Arg Cys Ser Ser Asn Ile Thr Gly Leu Leu Leu Thr Arg
        275                 280                 285

Asp Gly Gly Asn Ser Asn Asn Glu Ser Glu Ile Phe Arg Pro Gly Gly
    290                 295                 300

Gly Asp Met Arg Asp Asn Trp Arg Ser Glu Leu Tyr Lys Tyr Lys Val
305                 310                 315                 320

Val Lys Ile Glu Pro Leu Gly Val Ala Pro Thr Lys Ala Lys
                325                 330

<210> SEQ ID NO 12
<211> LENGTH: 1019
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 12

```
ccatggctac agaaaaattg tgggtcacag tctattatgg ggtacctgtg tggaaggaag      60
caaccaccac tctattttgt gcatcagatg ctaaagcata tgatacagag gtacataatg     120
tttgggccac acatgcctgt gtacccacag accccaaccc acaagaagta gtattgagct     180
gcaacacctc tgtcattaca caggcctgtc caaaggtatc ctttgagcca attcccatac     240
attattgtgc cccggctggt tttgcgattc taaaatgtaa taataagacg ttcaatggaa     300
caggaccatg tacaaatgtc agcacagtac aatgtacaca tggaattagg ccagtagtat     360
caactcaact gctgttaaat ggcagtctag cagaagaaga ggtagtaatt agatctgtca     420
atttcacgga caatgctaaa accataatag tacagctgaa cacatctgta gaaattaatt     480
gtacacattg taacattagt agagcaaaat ggaataacac tttaaaacag atagctagca     540
aattaagaga acaatttgga aataataaaa caataatctt taagcaatcc tcaggagggg     600
acccagaaat tgtaacgcac agttttaatt gtggagggga attttctac tgtaattcaa     660
cacaactgtt taatagtact tggtttaata gtacttggag tactgaaggg tcaaataaca     720
ctgaaggaag tgacacaatc accctcccat gcagaataaa acaaattata aacatgtggc     780
agaaagtagg aaaagcaatg tatgcccctc ccatcagtgg acaaattaga tgttcatcaa     840
atattacagg gctgctatta acaagagatg gtggtaatag caacaatgag tccgagatct     900
tcagacctgg aggaggagat atgagggaca attggagaag tgaattatat aaatataaag     960
tagtaaaaat tgaaccatta ggagtagcac ccaccaaggc aaagtgataa ctggatcct    1019
```

<210> SEQ ID NO 13
<211> LENGTH: 356
<212> TYPE: PRT
<213> ORGANISM: Artificial Sequence
<220> FEATURE:
<223> OTHER INFORMATION: Description of Artificial Sequence: Synthetic construct

<400> SEQUENCE: 13

```
Met Ala Thr Glu Lys Leu Trp Val Thr Val Tyr Tyr Gly Val Pro Val
 1               5                  10                  15

Trp Lys Glu Ala Thr Thr Thr Leu Phe Cys Ala Ser Asp Ala Lys Ala
            20                  25                  30

Tyr Asp Thr Glu Val His Asn Val Trp Ala Thr His Ala Cys Val Pro
        35                  40                  45

Thr Asp Pro Asn Pro Gln Glu Val Val Leu Ser Cys Asn Thr Ser Val
    50                  55                  60

Ile Thr Gln Ala Cys Pro Lys Val Ser Phe Glu Pro Ile Pro Ile His
65                  70                  75                  80

Tyr Cys Ala Pro Ala Gly Phe Ala Ile Leu Lys Cys Asn Asn Lys Thr
                85                  90                  95

Phe Asn Gly Thr Gly Pro Cys Thr Asn Val Ser Thr Val Gln Cys Thr
            100                 105                 110

His Gly Ile Arg Pro Val Val Ser Thr Gln Leu Leu Leu Asn Gly Ser
        115                 120                 125

Leu Ala Glu Glu Glu Val Val Ile Arg Ser Val Asn Phe Thr Asp Asn
    130                 135                 140

Ala Lys Thr Ile Ile Val Gln Leu Asn Thr Ser Val Glu Ile Asn Cys
145                 150                 155                 160
```

-continued

```
Thr His Cys Asn Ile Ser Arg Ala Lys Trp Asn Asn Thr Leu Lys Gln
            165                 170                 175

Ile Ala Ser Lys Leu Arg Glu Gln Phe Gly Asn Asn Lys Thr Ile Ile
        180                 185                 190

Phe Lys Gln Ser Ser Gly Gly Asp Pro Glu Ile Val Thr His Ser Phe
    195                 200                 205

Asn Cys Gly Gly Glu Phe Phe Tyr Cys Asn Ser Thr Gln Leu Phe Asn
210                 215                 220

Ser Thr Trp Phe Asn Ser Thr Trp Ser Thr Glu Gly Ser Asn Asn Thr
225                 230                 235                 240

Glu Gly Ser Asp Thr Ile Thr Leu Pro Cys Arg Ile Lys Gln Ile Ile
                245                 250                 255

Asn Met Trp Gln Lys Val Gly Lys Ala Met Tyr Ala Pro Pro Ile Ser
            260                 265                 270

Gly Gln Ile Arg Cys Ser Ser Asn Ile Thr Gly Leu Leu Leu Thr Arg
        275                 280                 285

Asp Gly Gly Asn Ser Asn Asn Glu Ser Glu Ile Phe Arg Pro Gly Gly
    290                 295                 300

Gly Asp Met Arg Asp Asn Trp Arg Ser Glu Leu Tyr Lys Tyr Lys Val
305                 310                 315                 320

Val Lys Ile Glu Pro Leu Gly Val Ala Pro Thr Lys Ala Lys Leu Asp
                325                 330                 335

Pro Asn Ser Ser Ser Val Asp Lys Leu Ala Ala Ala Leu Glu His His
            340                 345                 350

His His His His
        355
```

<210> SEQ ID NO 14
<211> LENGTH: 1073
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
ccatggctac agaaaaattg tgggtcacag tctattatgg ggtacctgtg tggaaggaag      60
caaccaccac tctattttgt gcatcagatg ctaaagcata tgatacagag gtacataatg     120
tttgggccac acatgcctgt gtacccacag accccaaccc acaagaagta gtattgagct     180
gcaacacctc tgtcattaca caggcctgtc aaaggtatc ctttgagcca attcccatac      240
attattgtgc cccggctggt tttgcgattc taaaatgtaa taataagacg ttcaatggaa     300
caggaccatg tacaaatgtc agcacagtac aatgtacaca tggaattagg ccagtagtat     360
caactcaact gctgttaaat ggcagtctag cagaagaaga ggtagtaatt agatctgtca     420
atttcacgga caatgctaaa accataatag tacagctgaa cacatctgta gaaattaatt     480
gtacacattg taacattagt agagcaaaat ggaataacac tttaaaacag atagctagca     540
aattaagaga acaatttgga aataataaaa caataatctt taagcaatcc tcaggagggg     600
acccagaaat tgtaacgcac agttttaatt gtggagggga attttctac tgtaattcaa      660
cacaactgtt taatagtact tggtttaata gtacttggag tactgaaggg tcaaataaca     720
ctgaaggaag tgacacaatc accctcccat gcagaataaa acaaattata aacatgtggc     780
agaaagtagg aaaagcaatg tatgccctc ccatcagtgg acaaattaga tgttcatcaa      840
atattacagg gctgctatta acaagagatg gtggtaatag caacaatgag tccgagatct     900
```

```
tcagacctgg aggaggagat atgagggaca attggagaag tgaattatat aaatataaag    960
tagtaaaaat tgaaccatta ggagtagcac ccaccaaggc aaagctggat ccgaattcga   1020
gctccgtcga caagcttgcg gccgcactcg agcaccacca ccaccaccac tga          1073
```

<210> SEQ ID NO 15
<211> LENGTH: 365
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

```
Met Ala Thr Glu Lys Leu Trp Val Thr Val Tyr Tyr Gly Val Pro Val
 1               5                  10                  15

Trp Lys Glu Ala Thr Thr Thr Leu Phe Cys Ala Ser Asp Ala Lys Ala
            20                  25                  30

Tyr Asp Thr Glu Val His Asn Val Trp Ala Thr His Ala Cys Val Pro
        35                  40                  45

Thr Asp Pro Asn Pro Gln Glu Val Val Leu Ser Cys Asn Thr Ser Val
    50                  55                  60

Ile Thr Gln Ala Cys Pro Lys Val Ser Phe Glu Pro Ile Pro Ile His
65                  70                  75                  80

Tyr Cys Ala Pro Ala Gly Phe Ala Ile Leu Lys Cys Asn Asn Lys Thr
                85                  90                  95

Phe Asn Gly Thr Gly Pro Cys Thr Asn Val Ser Thr Val Gln Cys Thr
            100                 105                 110

His Gly Ile Arg Pro Val Val Ser Thr Gln Leu Leu Leu Asn Gly Ser
        115                 120                 125

Leu Ala Glu Glu Glu Val Val Ile Arg Ser Val Asn Phe Thr Asp Asn
    130                 135                 140

Ala Lys Thr Ile Ile Val Gln Leu Asn Thr Ser Val Glu Ile Asn Cys
145                 150                 155                 160

Thr His Cys Asn Ile Ser Arg Ala Lys Trp Asn Asn Thr Leu Lys Gln
                165                 170                 175

Ile Ala Ser Lys Leu Arg Glu Gln Phe Gly Asn Asn Lys Thr Ile Ile
            180                 185                 190

Phe Lys Gln Ser Ser Gly Gly Asp Pro Glu Ile Val Thr His Ser Phe
        195                 200                 205

Asn Cys Gly Gly Glu Phe Phe Tyr Cys Asn Ser Thr Gln Leu Phe Asn
    210                 215                 220

Ser Thr Trp Phe Asn Ser Thr Trp Ser Thr Glu Gly Ser Asn Asn Thr
225                 230                 235                 240

Glu Gly Ser Asp Thr Ile Thr Leu Pro Cys Arg Ile Lys Gln Ile Ile
                245                 250                 255

Asn Met Trp Gln Lys Val Gly Lys Ala Met Tyr Ala Pro Pro Ile Ser
            260                 265                 270

Gly Gln Ile Arg Cys Ser Ser Asn Ile Thr Gly Leu Leu Leu Thr Arg
        275                 280                 285

Asp Gly Gly Asn Ser Asn Asn Glu Ser Glu Ile Phe Arg Pro Gly Gly
    290                 295                 300

Gly Asp Met Arg Asp Asn Trp Arg Ser Glu Leu Tyr Lys Tyr Lys Val
305                 310                 315                 320

Val Lys Ile Glu Pro Leu Gly Val Ala Pro Thr Lys Ala Lys Leu Asp
```

```
                    325                 330                 335
Pro Asn Ser Ser Ser Val Asp Lys Leu Ala Ala Ala Val Val His Phe
            340                 345                 350

Phe Lys Asn Ile Val Thr Pro Arg Thr Pro Pro Ser
        355                 360                 365

<210> SEQ ID NO 16
<211> LENGTH: 1106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ccatggctac agaaaaattg tgggtcacag tctattatgg ggtacctgtg tggaaggaag      60
caaccaccac tctattttgt gcatcagatg ctaaagcata tgatacagag gtacataatg    120
tttgggccac acatgcctgt gtacccacag accccaaccc acaagaagta gtattgagct    180
gcaacacctc tgtcattaca caggcctgtc caaaggtatc ctttgagcca attcccatac    240
attattgtgc cccggctggt tttgcgattc taaaatgtaa taataagacg ttcaatggaa    300
caggaccatg tacaaatgtc agcacagtac aatgtacaca tggaattagg ccagtagtat    360
caactcaact gctgttaaat ggcagtctag cagaagaaga ggtagtaatt agatctgtca    420
atttcacgga caatgctaaa accataatag tacagctgaa cacatctgta gaaattaatt    480
gtacacattg taacattagt agagcaaaat ggaataacac tttaaaacag atagctagca    540
aattaagaga acaatttgga aataataaaa caataatctt taagcaatcc tcaggagggg    600
acccagaaat tgtaacgcac agttttaatt gtggagggga ttttttctac tgtaattcaa    660
cacaactgtt taatagtact tggtttaata gtacttggag tactgaaggg tcaaataaca    720
ctgaaggaag tgacacaatc accctcccat gcagaataaa acaaattata aacatgtggc    780
agaaagtagg aaaagcaatg tatgcccctc ccatcagtgg acaaattaga tgttcatcaa    840
atattacagg gctgctatta acaagagatg gtggtaatag caacaatgag tccgagatct    900
tcagacctgg aggaggagat atgagggaca attggagaag tgaattatat aaatataaag    960
tagtaaaaat tgaaccatta ggagtagcac ccaccaaggc aaagctggat ccgaattcga   1020
gctccgtcga caagcttgcg gccgcagtag tccatttctt caagaacatt gtgacacctc   1080
gaacaccacc tccatcctaa ctcgag                                         1106

<210> SEQ ID NO 17
<211> LENGTH: 384
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 17

Met Ala Thr Glu Lys Leu Trp Val Thr Val Tyr Tyr Gly Val Pro Val
  1               5                  10                  15

Trp Lys Glu Ala Thr Thr Thr Leu Phe Cys Ala Ser Asp Ala Lys Ala
             20                  25                  30

Tyr Asp Thr Glu Val His Asn Val Trp Ala Thr His Ala Cys Val Pro
         35                  40                  45

Thr Asp Pro Asn Pro Gln Glu Val Val Leu Ser Cys Asn Thr Ser Val
     50                  55                  60
```

```
Ile Thr Gln Ala Cys Pro Lys Val Ser Phe Glu Pro Ile Pro Ile His
 65                  70                  75                  80

Tyr Cys Ala Pro Ala Gly Phe Ala Ile Leu Lys Cys Asn Asn Lys Thr
                 85                  90                  95

Phe Asn Gly Thr Gly Pro Cys Thr Asn Val Ser Thr Val Gln Cys Thr
            100                 105                 110

His Gly Ile Arg Pro Val Val Ser Thr Gln Leu Leu Asn Gly Ser
        115                 120                 125

Leu Ala Glu Glu Glu Val Val Ile Arg Ser Val Asn Phe Thr Asp Asn
130                 135                 140

Ala Lys Thr Ile Ile Val Gln Leu Asn Thr Ser Val Glu Ile Asn Cys
145                 150                 155                 160

Thr His Cys Asn Ile Ser Arg Ala Lys Trp Asn Asn Thr Leu Lys Gln
                165                 170                 175

Ile Ala Ser Lys Leu Arg Glu Gln Phe Gly Asn Asn Lys Thr Ile Ile
            180                 185                 190

Phe Lys Gln Ser Ser Gly Gly Asp Pro Glu Ile Val Thr His Ser Phe
        195                 200                 205

Asn Cys Gly Gly Glu Phe Phe Tyr Cys Asn Ser Thr Gln Leu Phe Asn
210                 215                 220

Ser Thr Trp Phe Asn Ser Thr Trp Ser Thr Glu Gly Ser Asn Asn Thr
225                 230                 235                 240

Glu Gly Ser Asp Thr Ile Thr Leu Pro Cys Arg Ile Lys Gln Ile Ile
                245                 250                 255

Asn Met Trp Gln Lys Val Gly Lys Ala Met Tyr Ala Pro Pro Ile Ser
            260                 265                 270

Gly Gln Ile Arg Cys Ser Ser Asn Ile Thr Gly Leu Leu Leu Thr Arg
        275                 280                 285

Asp Gly Gly Asn Ser Asn Asn Glu Ser Glu Ile Phe Arg Pro Gly Gly
290                 295                 300

Gly Asp Met Arg Asp Asn Trp Arg Ser Glu Leu Tyr Lys Tyr Lys Val
305                 310                 315                 320

Val Lys Ile Glu Pro Leu Gly Val Ala Pro Thr Lys Ala Lys Leu Asp
                325                 330                 335

Pro His His His His His Gly Ser Gly Glu Gln Lys Leu Ile Ser
            340                 345                 350

Glu Glu Asp Leu Asn Ser Ser Ser Val Asp Lys Leu Ala Ala Ala Val
        355                 360                 365

Val His Phe Phe Lys Asn Ile Val Thr Pro Arg Thr Pro Pro Ser
    370                 375                 380

<210> SEQ ID NO 18
<211> LENGTH: 1163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
ccatggctac agaaaaattg tgggtcacag tctattatgg ggtacctgtg tggaaggaag      60
caaccaccac tctatttttgt gcatcagatg ctaaagcata tgatacagag gtacataatg    120
tttgggccac acatgcctgt gtacccacag accccaaccc acaagaagta gtattgagct    180
gcaacacctc tgtcattaca caggcctgtc caaaggtatc ctttgagcca attcccatac    240
```

```
attattgtgc cccggctggt tttgcgattc taaaatgtaa taataagacg ttcaatggaa      300
caggaccatg tacaaatgtc agcacagtac aatgtacaca tggaattagg ccagtagtat      360
caactcaact gctgttaaat ggcagtctag cagaagaaga ggtagtaatt agatctgtca      420
atttcacgga caatgctaaa accataatag tacagctgaa cacatctgta gaaattaatt      480
gtacacattg taacattagt agagcaaaat ggaataacac tttaaaacag atagctagca      540
aattaagaga acaatttgga ataataaaa caataatctt taagcaatcc tcaggagggg      600
acccagaaat tgtaacgcac agttttaatt gtggagggga attttctac tgtaattcaa       660
cacaactgtt taatagtact tggtttaata gtacttggag tactgaaggg tcaaataaca      720
ctgaaggaag tgacacaatc accctcccat gcagaataaa acaaattata acatgtggc       780
agaaagtagg aaaagcaatg tatgcccctc ccatcagtgg acaaattaga tgttcatcaa      840
atattcagg gctgctatta acaagagatg gtggtaatag caacaatgag tccgagatct       900
tcagacctgg aggaggagat atgagggaca attggagaag tgaattatat aaatataaag     960
tagtaaaaat tgaaccatta ggagtagcac ccaccaaggc aaagctggat ccgcaccacc     1020
accaccacca cggttccggt gaacaaaaac tcatctcaga agaggatctg aattcgagct     1080
ccgtcgacaa gcttgcggcc gcagtagtcc atttcttcaa gaacattgtg acacctcgaa     1140
caccacctcc atcctaactc gag                                             1163
```

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Asp Pro Asn Asn Ser Ser Ser Val Asp Lys Leu Ala Ala Ala Leu
1               5                   10                  15

Glu

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Asp Pro Asn Asn Ser Ser Ser Val Asp Lys Leu Ala Ala Ala
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Ser Ser Ser Val Asp Lys Leu Ala Ala Ala
1               5                   10

<210> SEQ ID NO 22

-continued

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6x-His tag

<400> SEQUENCE: 22

His His His His His His
  1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Ala Glu Glu Glu Val
  1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: (t-Bu)Glu

<400> SEQUENCE: 24

Val Ala Glu Glu Glu
  1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Ala Glu Glu Glu Val
  1               5
```

METHOD FOR PRODUCING CATALYTIC ANTIBODIES (VARIANTS), ANTIGENS FOR IMMUNIZATION AND NUCLEOTIDE SEQUENCE

This application is a continuation-in-part of application Ser. No. 10/475,706, filed May 12, 2004, which is a 371 National Stage application of International application no. PCT/RU02/00177, filed Apr. 18, 2002, now abandoned which claims priority to Russian application no. 2001110759, filed Apr. 24, 2001. The entire contents of the above-referenced applications are hereby incorporated by reference in their entirety.

FIELD OF THE INVENTION

The present invention relates to biotechnology, immunology, genetic engineering, the microbiological and medicinal industries and comprises a combined approach to the manufacture and expression of catalytically active antibodies which are potential therapeuticals intended to destroy protein antigens, in particular gp120, which is the main surface protein of human immunodeficiency virus.

PRIOR ART

It is known that catalytic antibodies targeted to physiologically active substances and natural objects useful in biomedicine may be designed as specific representations of transition states of modeled chemical conversions. U.S. Pat. No. 5,948,658 discloses an antibody designed by the above approach and capable of specifically cleaving narcotic cocaine. In spite of a highly developed technology for the production of monoclonal antibodies, this approach cannot be effective in the case of high molecular biopolymers, proteins, and peptides because it is difficult to model corresponding transition states of the reaction.

The production of catalytic antibodies directly active against gp120 is disclosed in WO 9703696; however, according to WO 9703696, the antibody is obtained from patient blood serum, which impedes development of a unified medical technology for medical drug production.

SUMMARY OF THE INVENTION

The object of the present invention is to develop a method for producing catalytic antibodies against proteins and peptides, in particular gp120, with the use of animals with spontaneous and inducible autoimmune pathologies, which method will make it possible to design a "catalytic vaccine" which, upon injection to a patient, is capable not only of binding the antigen but also of destroying it thus inhibiting the development of disease.

According to one embodiment, the present invention provides a method for producing catalytic antibodies with the use of animals genetically predisposed to develop spontaneous and induced autoimmune pathologies. Mice are used as the animals with spontaneous and inducible autoimmune pathologies. The used mice belong to strains for which immunization with myelin basic protein or its fragments designated in the literature as "encephalitogenic peptides" or "encephalitogenic epitopes" can induce the development of experimental autoimmune encephalomyelitis. The animals are administered with a fusion protein consisting of myelin basic protein or its fragments and a potential substrate of catalytic antibody or a fragment of the potential substrate. The potential substrate is gp120 (surface glycoprotein of HIV-1) or its fragments. In the present invention also provided variants of chimeric proteins containing the fragments of the gp120. These proteins are used as antigenic substrates to elicit the abovementioned catalytic antibody. Also said antigenic substrates can be used as immunogens to elicit binding/neutralizing antibodies The present invention provides a protein comprising amino acid sequence (I) (SEQ ID NO: 1):

TEKLWVTVYYGVPVWKEATTTLFCASDAKAYDTEVHNVWATHACVPTDPN

PQEVVLSCNTSVITQACPKVSFEPIPIHYCAPAGFAILKCNNKTFNGTGP

CTNVSTVQCTHGTRPVVSTQLLLNGSLAEEEVVIRSVNFTDNAKTIIVQL

NTSVEINCTHCNISRAKWNNTLKQIASKLREQFGNNKTIIFKQSSGGDPE

IVTHSFNCGGEFFYCNSTQLFNSTWFNSTWSTEGSNNTEGSDTITLPCRI

KQIINMWQKVGKAMYAPPISGQIRCSSNITGLLLTRDGGNSNNESEIFRP

GGGDMRDNWRSELYKYKVVKIEPLGVAPTKAK

The present invention also provides as a variant of the abovementioned protein comprising amino acid sequence (I) a fusion protein having the following common amino acide sequence structure (II): $Z_1$—X—$Z_2$, wherein $Z_1$ is a sequence of from 0 to 19 amino acid residues and $Z_2$ are a sequence of from 0 to 50 amino acid residues, and if $Z_1$ or $Z_2$=zero amino acid residues, then $Z_1$=—H (hydrogen) and/or $Z_2$=—OH (hydroxyl group); and X is the amino acid sequence (I).

$Z_1$ may be presented by a pair of amino acids, for example, by Met-Ala or a sequence of amino acids facilitating secretion of the said protein to the extracellular space ("signal sequence"); for example, it may be bacteriophage pIII periplasmic signal 18-amino acid sequence (i.e. MKKLLFAIPL-WPFYSHS) (SEQ ID NO: 2) or antibody heavy chain 19-amino acid signal peptide (i.e MNFGLRLIFLV-LTLKGVQC) (SEQ ID NO: 3).

$Z_2$ may be presented by a short protein containing, for example, histidine clusters and/or the fragments of Myelin Basic Protein (MBP).

Preferred $Z_2$ amino acid sequences are the following:

LDPNSSSVDKLAAALEHHHHHH (SEQ ID NO: 4) (this 22-amino acid sequence comprises, for example, flexible polylinker and 6-histidine cluster); LDPNSSSVDK-LAAAVVHFFKNIVTPRTPPPS (SEQ ID NO: 5) (this 31-amino acid sequence comprises, for example, polylinker and a part of amino acid sequence of MBP (particularly, VVHFFKNIVTPRTPPPS) (SEQ ID NO: 6); LDPHHHHHH (SEQ ID NO: 7) (this 9-amino acid sequence comprises, for example, short polylinker and histidine cluster); GSGEQK-LISEEDLNSSSVDKLAAAVVHFFKNIVTPRTPPPS (SEQ ID NO: 8) (this 41-amino acid sequence comprises, for example, short polylinker GSG, 10—amino acid segment of immunodominant epytope of human c-myc 62 protein EQK-LISEEDL (SEQ ID NO: 9), a flexible [olylinker and a part of amino acid sequence of MBP (particularly, VVHFFKNIVTPRTPPPS) (SEQ ID NO: 6); LDPHHHHH-HGSGEQKLISEEDLNSSSVDKLAAAWH-FFKNIVTPRTPPPS (SEQ ID NO: 10) (this 50-amino acid sequence comprises, for example, two short rigid 3-amino acid linkers, 6-histidine cluster, 10—amino acid segment of immunodominant epytope of human c-myc 62 protein EQK-LISEEDL (SEQ ID NO: 9) a flexible polylinker and a part of amino acid sequence of MBP (particularly, VVHFFKNIVTPRTPPPS) (SEQ ID NO: 6).

As the variant of protein of common structure II the following fusion protein is provided by the invention (SEQ ID NO: 11):

MATEKLWVTVYYGVPVWKEATTTLFCASDAKAYDTEVHNVWATHACVPTD
PNPQEVVLSCNTSVITQACPKVSFEPIPIHYCAPAGFAILKCNNKTFNGT
GPCTNVSTVQCTHGIRPVVSTQLLLNGSLAEEEVVIRSVNFTDNAKTIIV
QLNTSVEINCTHCNTSRAKWNNTLKQIASKLREQFGNNKTIIFKQSSGGD
PEIVTHSFNCGGEFFYCNSTQLFNSTWFNSTWSTEGSNNTEGSDTITLPC
RIKQIINMWQKVGKAMYAPPISGQIRCSSNITGLLLTRDGGNSNNESEIF
RPGGGDMRDNWRSELYKYKVVKIEPLGVAPTKAK

This fusion protein is designated hereinafter also as product of Construct 16. Also the nucleotide sequence encoding the product of Construct 16 is provided by the invention (SEQ ID NO: 12):

*ccatgg*ctacagaaaaattgtgggtcacagtctattatggggtacctgtg
tggaaggaagcaaccaccactctattttgtgcatcagatgctaaagcata
tgatacagaggtacataatgtttgggccacacatgcctgtgtacccacag
accccaacccacaagaagtagtattgagctgcaacacctctgtcattaca
caggcctgtccaaaggtatcctttgagccaattcccatacattattgtgc
cccggctggttttgcgattctaaaatgtaataataagacgttcaatggaa
caggaccatgtacaaatgtcagcacagtacaatgtacacatggaattagg
ccagtagtatcaactcaactgctgttaaatggcagtctagcagaagaaga
ggtagtaattagatctgtcaatttcacggacaatgctaaaaccataatag
tacagctgaacacatctgtagaaattaattgtacacattgtaacattagt
agagcaaaatggaataacactttaaaacagatagctagcaaattaagaga
acaatttggaaataataaaacaataatctttaagcaatcctcaggaggg
acccagaaattgtaacgcacagttttaattgtggaggggaattttctac
tgtaattcaacacaactgtttaatagtacttggtttaatagtacttggag
tactgaagggtcaaataacactgaaggaagtgacacaatcaccctcccat
gcagaataaaacaaattataaacatgtggcagaaagtaggaaaagcaatg
tatgcccctcccatcagtggacaaattagatgttcatcaaatattacagg
gctgctattaacaagagatggtggtaatagcaacaatgagtccgagatct
tcagacctggaggaggagatatgagggacaattggagaagtgaattatat
aaatataaagtagtaaaaattgaaccattaggagtagcacccaccaaggc
aaagtgataact *ggatcc*t Also the another variant of protein of common structure II the following fusion protein is provided by the invention (SEQ ID NO: 13):

MATEKLWVTVYYGVPVWKEATTTLFCASDAKAYDTEVHNVWATHACVPTD
PNPQEVVLSCNTSVITQACPKVSFEPIPIHYCAPAGFAILKCNNKTFNGT
GPCTNVSTVQCTHGIRPVVSTQLLLNGSLAEEEVVIRSVNFTDNAKTIIV
QLNTSVEINCTHCNISRAKWNNTLKQIASKLREQFGNNKTIIFKQSSGGD
PEIVTHSFNCGGEFFYCNSTQLFNSTWFNSTWSTEGSNNTEGSDTITLPC
RIKQIINMWQKVGKAMYAPPISGQIRCSSNITGLLLTRDGGNSNNESEIF
RPCCGDMRDNWRSELYKYKVVKIEPLGVAPTKAKLDPNSSSVDKLAAALE
HHHHHH

This fusion protein is designated hereinafter also as the product of Construct 13.

Also the nucleotide sequence encoding the product of Construct 13 is provided by the invention (SEQ ID NO: 14):

ccatggctacagaaaaattgtgggtcacagtctattatggggtacctgtg
tggaaggaagcaaccaccactctattttgtgcatcagatgctaaagcata
tgatacagaggtacataatgtttgggccacacatgcctgtgtacccacag
accccaacccacaagaagtagtattgagctgcaacacctctgtcattaca
caggcctgtccaaaggtatcctttgagccaattcccatacattattgtgc
cccggctggttttgcgattctaaaatgtaataataagacgttcaatggaa
caggaccatgtacaaatgtcagcacagtacaatgtacacatggaattagg
ccagtagtatcaactcaactgctgttaaatggcagtctagcagaagaaga
ggtagtaattagatctgtcaatttcacggacaatgctaaaaccataatag
tacagctgaacacatctgtagaaattaattgtacacattgtaacattagt
agagcaaaatggaataacactttaaaacagatagctagcaaattaagaga
acaatttggaaataataaaacaataatctttaagcaatcctcaggagggg
acccagaaattgtaacgcacagttttaattgtggaggggaattttctac
tgtaattcaacacaactgtttaatagtacttggtttaatagtacttggag
tactgaagggtcaaataacactgaaggaagtgacacaatcaccctcccat
gcagaataaaacaaattataaacatgtggcagaaagtaggaaaagcaatg
tatgcccctcccatcagtggacaaattagatgttcatcaaatattacagg
gctgctattaacaagagatggtggtaatagcaacaatgagtccgagatct
tcagacctggaggaggagatatgagggacaattggagaagtgaattatat
aaatataaagtagtaaaaattgaaccattaggagtagcacccaccaaggc
aaagctggatccgaattcgagctccgtcgacaagcttgcggccgcactcg
agcaccaccaccaccactga Also the invention provides another variant of fusion protein of common structure II having the following amino acid sequence (SEQ ID NO: 15):

MATEKLWVTVYYGVPVWKEATTTLFCASDAKAYDTEVHNVWATHACVPTD
PNPQEVVLSCNTSVITQACPKVSFEPIPIHYCAPAGFAILKCNNKTFNGT
GPCTNVSTVQCTHGIRPVVSTQLLLNGSLAEEEVVIRSVNFTDNAKTIIV
QLNTSVEINCTHCNISRAKWNNTLKQIASKLREQFGNNKTIIFKQSSGGD
PEIVTHSFNCGGEFFYCNSTQLFNSTWFNSTWSTEGSNNTEGSDTITLPC
RIKQIINMWQKVGKAMYAPPISGQIRCSSNITGLLLTRDGGNSNNESEIF

-continued

RPGGGDMRDNWRSELYKYKVVKIEPLGVAPTKAKLDPNSSSVDKLAAAVV

HFFKNIVTPRTPPPS

This fusion protein is designated hereinafter also as product of Construct 14.

Also the nucleotide sequence encoding the product of the Construct 14 is provided by the invention (SEQ ID NO: 16):

ccatggctacagaaaaattgtgggtcacagtctattatggggtacctgtg tggaaggaagcaaccaccactctattttgtgcatcagatgctaaagcata tgatacagaggtacataatgtttgggccacacatgcctgtgtacccacag accccaacccacaagaagtagtattgagctgcaacacctctgtcattaca caggcctgtccaaaggtatcctttgagccaattcccatacattattgtgc cccggctggttttgcgattctaaaatgtaataataagacgttcaatggaa caggaccatgtacaaatgtcagcacagtacaatgtacacatggaattagg ccagtagtatcaactcaactgctgttaaatggcagtctagcagaagaaga ggtagtaattagatctgtcaatttcacggacaatgctaaaaccataatag tacagctgaacacatctgtagaaattaattgtacacattgtaacattagt agagcaaaatggaataacactttaaaacagatagctagcaaattaagaga acaatttggaaataataaaacaataatctttaagcaatcctcaggagggg acccagaaattgtaacgcacagttttaattgtggaggggaattttctac tgtaattcaacacaactgtttaatagtacttggtttaatagtacttggag tactgaagggtcaaataacactgaaggaagtgacacaatcaccctcccat gcagaataaaacaaattataaacatgtggcagaaagtaggaaaagcaatg tatgcccctcccatcagtggacaaattagatgttcatcaaatattacagg gctgctattaacaagagatggtggtaatagcaacaatgagtccgagatct tcagacctggaggaggagatatgagggacaattggagaagtgaattatat aaatataaagtagtaaaaattgaaccattaggagtagcacccaccaaggc aaagctggatccgaattcgagctccgtcgacaagcttgcggccgcagtag tccatttcttcaagaacattgtgacacctcgaacaccacctccatcctaa ctcgag Also the invention provides another variant of fusion protein of structure II which have the following amino acid sequence (SEQ ID NO: 17):

MATEKLWVTVYYGVPVWKEATTTLFCASDAKAYDTEVHNVWATHACVPTD

PNPQEVVLSCNTSVITQACPKVSFEPIPIHYCAPAGFAILKCNNKTFNGT

GPCTNVSTVQCTHGIRPVVSTQLLLNGSLAEEEVVIRSVNFTDNAKTIIV

QLNTSVEINCTHCNISRAKWNNTLKQIASKLREQFGNNKTIIFKQSSGGD

PEIVTHSFNCGGEFFYCNSTQLFNSTWFNSTWSTEGSNNTEGSDTITLPC

RIKQIINMWQKVGKAMYAPPISGQIRCSSNITGLLLTRDCGNSNNESEIF

RPGGGDMRDNWRSELYKYKVVKTEPLGVAPTKAKLDPHHHHHHGSGEQKL

ISEEDLNSSSVDKLAAAVVHFFKNTVTPRTPPPS

This fusion protein is designated hereinafter also as product of Construct 15 or gp120 I-IIImbp protein.

Also the nucleotide sequence encoding the product of the Construct 15 is provided by the invention (SEQ ID NO: 18):

```
ccatggctacagaaaaattgtgggtcacagtctattatggggtacctgtg
tggaaggaagcaaccaccactctattttgtgcatcagatgctaaagcata
tgatacagaggtacataatgtttgggccacacatgcctgtgtacccacag
accccaacccacaagaagtagtattgagctgcaacacctctgtcattaca
caggcctgtccaaaggtatcctttgagccaattcccatacattattgtgc
cccggctggttttgcgattctaaaatgtaataataagacgttcaatggaa
caggaccatgtacaaatgtcagcacagtacaatgtacacatggaattagg
ccagtagtatcaactcaactgctgttaaatggcagtctagcagaagaaga
ggtagtaattagatctgtcaatttcacggacaatgctaaaaccataatag
tacagctgaacacatctgtagaaattaattgtacacattgtaacattagt
agagcaaaatggaataacactttaaaacagatagctagcaaattaagaga
acaatttggaaataataaaacaataatctttaagcaatcctcaggagggg
acccagaaattgtaacgcacagttttaattgtggaggggaatttttctac
tgtaattcaacacaactgtttaatagtacttggtttaatagtacttggag
tactgaagggtcaaataacactgaaggaagtgacacaatcaccctcccat
gcagaataaaacaaattataaacatgtggcagaaagtaggaaaagcaatg
tatgcccctcccatcagtggacaaattagatgttcatcaaatattacagg
gctgctattaacaagagatggtggtaatagcaacaatgagtccgagatct
tcagacctggaggaggagatatgagggacaattggagaagtgaattatat
aaatataaagtagtaaaaattgaaccattaggagtagcacccaccaaggc
aaagctggatccgcaccaccaccaccaccacggttccggtgaacaaaaac
tcatctcagaagaggatctgaattcgagctccgtcgacaagcttgcggcc
gcagtagtccatttcttcaagaacattgtgacacctcgaacaccacctcc
atcctaactcgag
```

The invention also provides a method of eliciting antibodies against gp120 glycoprotein of human immunodeficiency virus comprising administering of abovementioned proteins containing in their structure the amino acid sequence (I).

According to its another embodiment, the present invention provides a method of eliciting catalytic antibodies against gp120 glycoprotein of human immunodeficiency virus by administering to mouse of SGL strain the product construct 15 (also designated hereinafter as protein gp120 I-IIImbp or as fusion protein gp120 I-IIImbp or as gp120 I-IIImbp).

This protein (protein gp120 I-IIImbp) comprises amino acid sequence (I), immunogenic epitope of immunodominant epitope of human p62 c-myc protein (i.e amino acid sequence EQKLISEEDL) (SEQ ID NO: 9) and the 89-104 peptide of the myelin basic protein (MBP) (i.e. amino acid sequence VVHFFKNIVTPRTPPPS (SEQ ID NO: 6). The SJL mouse strain is widely used as an animal model for experimental autoimmune encephalitis (EAE) (see, for example, Liedtke W et al, Effective treatment of models of multiple sclerosis by matrix metalloproteinase inhibitors *Annals of Neurology,* 1998, July; vol., 44(N1), pp. 35-46).

As a variant of said inventive method SJL mice are immunized with an antigen containing a haptene, the hapten being a conjugate of a mechanism-dependent covalent protease inhibitor with a peptide, the peptide being a gp120 or its fragment or its fragments (substrate of the catalytic antibody).

The hapten and its isomers and racemates used in the variant of the method of the present invention have the following structure (SEQ ID NO: 23):

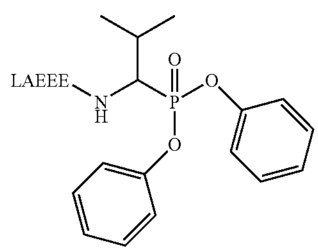

BRIEF DESCRIPTION OF THE DRAWINGS

FIG. 1A/1. Nucleotide sequence of Construct 16 (SEQ ID NO: 12).

NcoI-BamHI fragment of gp120I-III is underlined by thin firm line. NcoI, BamHI restriction sites are highlighted by bold italic type. The pET plasmid fragment comprising polylinker and histidine cluster is highlighted by double line.

FIG. 1A/2. Amino acid sequence of product of Construct 16 (SEQ ID NO: 11).

The fragment gp120 I-III is underlined: fragment I is highlighted by firm thin line; fragment II is highlighted by wavy line; fragment III is highlighted by double line.

FIG. 1B/1. Nucleotide sequence of Construct 13 (SEQ ID NO: 14).

NcoI-BamHI fragment of gp120I-III is underlined by thin firm line. NcoI and BamHI restriction sites are highlighted by bold italic type. The pET plasmid fragment comprising polylinker and histidine cluster is highlighted by double line.

FIG. 1B/2. Amino acid sequence of product of Construct 13 (SEQ ID NO: 13). The fragment gp 120 I-III is underlined: fragment I is highlighted by firm thin line; fragment II is highlighted by wavy line; fragment III is highlighted by double line. The histidine cluster is highlighted by bold type. Unhighlighted sequence LDPNNSSS-VDKLAAALE (SEQ ID NO: 19) is a flexible linker.

FIG. 1C/1. Nucleotide sequence of Construct 14 (SEQ ID NO: 16). NcoI-BamHI fragment of gp120I-III is underlined by thin line. NcoI, BamHI, EcoRI, NotI and XhoI restriction sites are highlighted by bold italic type. The pET plasmid fragment comprising polylinker is highlighted by double line. The NotI-XhoI fragment coding of MBP amino acid fragment, is highlighted by thick line and highlighted by bold type.

FIG. 1C/2. Amino acid sequence of product of Construct 14 (SEQ ID NO: 15). The fragment gp 120 I-III is underlined: fragment I is highlighted by firm thin line; fragment II is highlighted by wavy line; fragment III is highlighted by double line. The MBP fragment is highlighted by thick firm line and bold type. Unhighlighted sequence LDPNNSSSVD-KLAAA (SEQ ID NO: 20) is a flexible polylinker.

FIG. 1D/1. Nucleotide sequence of Construct 15 (gp120 I-IIImbp protein) (SEQ ID NO: 18). NcoI-BamHI fragment of gp120I-III is underlined by thin line. NcoI, BamHI, EcoRI, NotI and XhoI restriction sites are highlighted by bold italic type. The pET plasmid fragment comprising polylinker is highlighted by double line. The fragment coding histidine cluster is highlighted by bold type. The sequence coding the epitope of c62-myc protein is highlighted by thin line and italicized. The NotI-XhoI fragment coding of MBP amino acid fragment, is highlighted by thick line and highlighted by bold type.

FIG. 1D/2. Amino acid sequence of product of Construct 15 (SEQ ID NO: 17) (fusion protein gp120 I-IIImbp protein). The fragment gp120 I-III is underlined: fragment I is highlighted by firm thin line; fragment II is highlighted by wavy line; fragment III is highlighted by double line.

The histidine cluster is highlighted by bold type. The epitope of c62-myc protein is highlighted by bold italic type. The MBP fragment is highlighted by thick firm line and bold type. Unhighlighted sequence LDP is a rigid linker. Unhighlighted sequence GSG is a flexible linker. Unhighlighted sequence NSSSVDKLAAA (SEQ ID NO: 21) is a flexible linker.

FIG. 2. Diagrams of constructs obtained with the use of pET32b vector and used for production of corresponding recombinant protein product. Hexahistidine tag disclosed as SEQ ID NO: 22.

FIG. 3. Diagrams of constructs obtained with the use of pET28a vector and used for production of corresponding recombinant protein product. Hexahistidine, EQKLISEEDL and VVHFFKNIVTPRTPPPS sequences disclosed as SEQ ID NOS 22, 9 and 6 respectively.

FIG. 4. Electrophoregram (A) and immunoblot (B) of different stages of isolation and purification of the protein gp120I-IIImbp (the product of Construct 15). 1—total cellular proteins before induction; 2—total cellular proteins after induction; 3—the fraction of soluble intracellular proteins; 4—soluble proteins not retained by the metal chelate column; 5—soluble proteins eluted at pH 5.0; 6—soluble protein form preparation after chromatographic purification; 7—the fraction of insoluble intracellular proteins; 8—insoluble proteins not retained by metal chelate column; 9—denaturated protein form preparation after chromatographic purification; 10—marker.

FIG. 5. Analysis of the antigen specificity of antibodies in blood serum of SJL mice (FIG. 5A) or BALB/c (FIG. 5B) immunized with the various prepared chimeric protein products at different doses. SJL-2 and BALB/c-1 are mice immunized with the dose of 150 μg per mouse, SJL-3 and BALB/c-2 are mice immunized with the dose of 300 μg per mouse. Group of bars I-II indicates that mice were immunized with peptide containing fragments I-II of gp120; group II-III indicates that immunization was done with the peptide containing fragments II-III of gp120; group III indicates results of immunization obtained with the peptide containing fragment III of gp120; group I-III indicates results of immunization obtained with the peptide containing fragments I-III of gp120

FIG. 6. The principles of fluorescent and enzymic analyses of proteolytic activity.

FIG. 7. Determination of the proteolytic activity of antibody preparation isolated from blood serum of SJL mice immunized with the fusion protein gp120I-IIImbp. SJL-1 are control mice. SJL-2 are mice immunized with the dose of 150 μg per mouse. SJL-3 are mice immunized with the dose of 300 μg per mouse. BSA-FITC and gp120-FITC were used as substrates.

FIG. 8. Inhibition of the proteolytic activity of antibody preparation isolated from blood serum of SJL mice immunized with the fusion protein gp120I-IIImbp. SJL-1 are control mice. SJL-2 are mice immunized with the dose of 150 μg per mouse.

AEBSF: aminoethanebenzenesulfonyl fluoride.

CMC: phenylalanylchloromethylketone.

Figure 9:
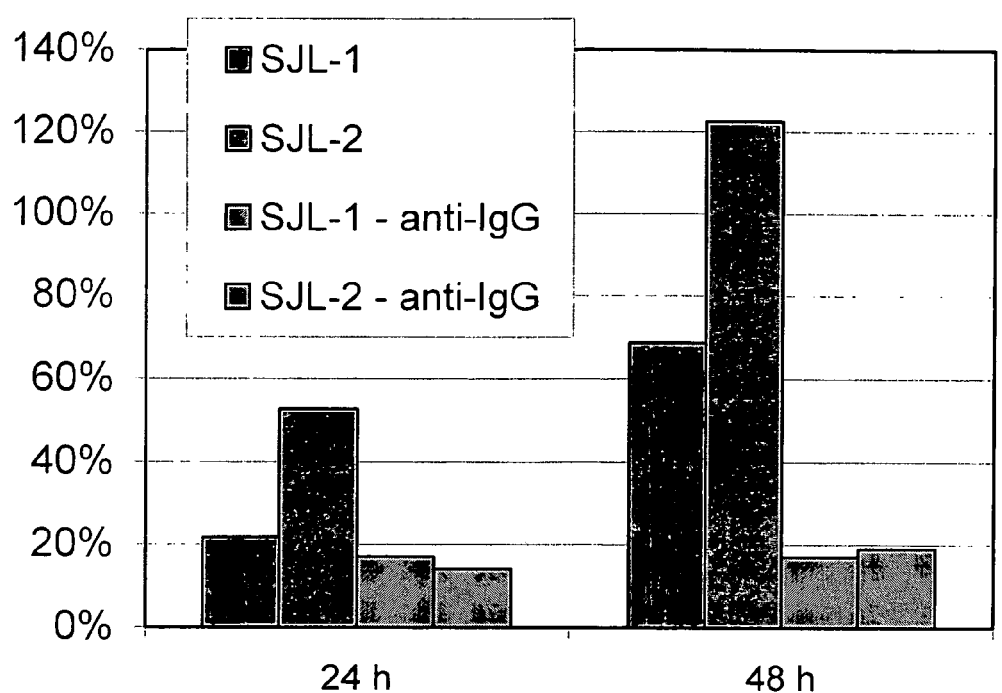

FIG. 9. Antispecies antibody inhibition of the proteolytic activity of antibody preparation isolated from blood serum of SJL mice immunized with the fusion protein gp120I-IIImbp. SJL-1 are control mice. SJL-2 are mice immunized with the dose of 150 μg per mouse.

Anti-IgG: rabbit polyclonal antibodies against murine IgG.

Figure 10:
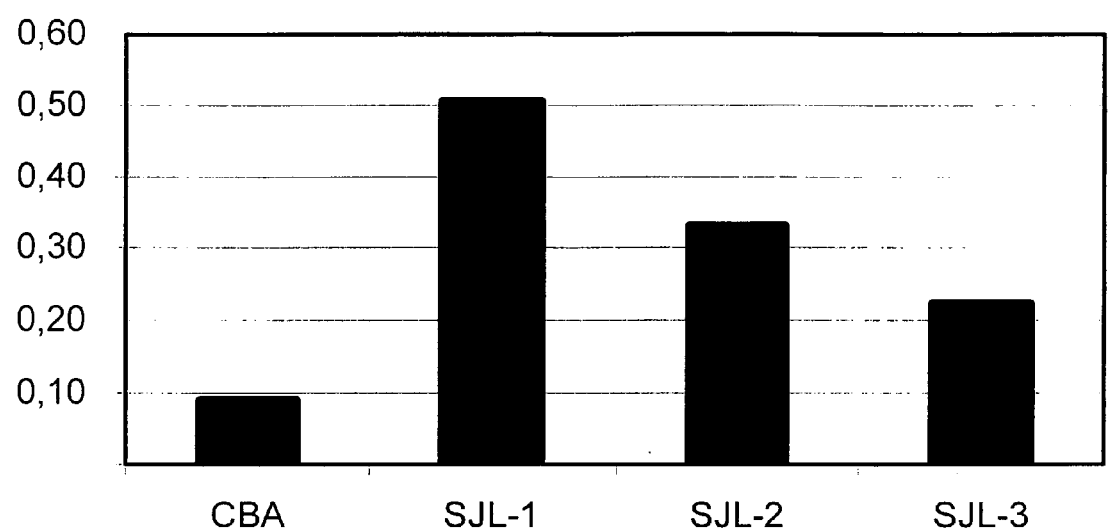

FIG. 10. Enzymatic determination of the proteolytic activity of antibody preparations isolated from blood sera of SJL mice immunized with the fusion protein gp120I-IIImbp at different doses. A: SJL-1 are control mice; SJL-2 are mice immunized with the dose of 150 μg per mouse; SJL-3 are mice immunized with the dose of 300 μg per mouse; CBA are control CBA mice.

Figure 11:
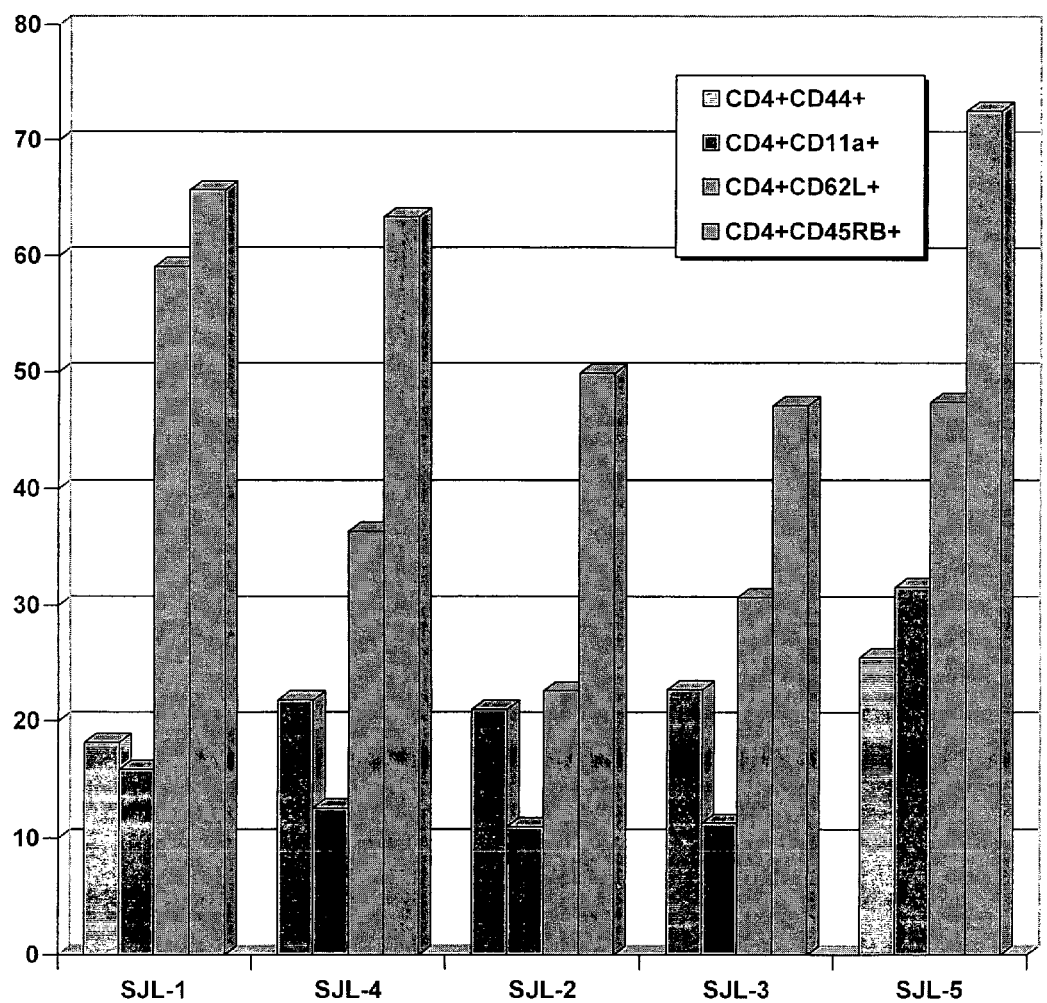

FIG. 11. Changes in the expression level of surface markers of T-cells of the immune system of SJL mice immunized with the fusion protein gp120I-IIImbp at different doses, with the recombinant protein gp120I-III, and with the encephalitogenic peptide MBP$_{89-104}$. SJL-1 are non-immunized mice. SJL-2 are mice immunized with gp120I-IIImbp at the dose of 150 μg per mouse. SJL-3: mice immunized with gp120I-IIImbp at the dose of 300 μg per mouse. SJL-4 are mice immunized with the peptide MBP$_{89-104}$. SJL-5 are mice immunized with the recombinant protein gp120I-III at the dose of 300 μg per mouse.

Figure 12:
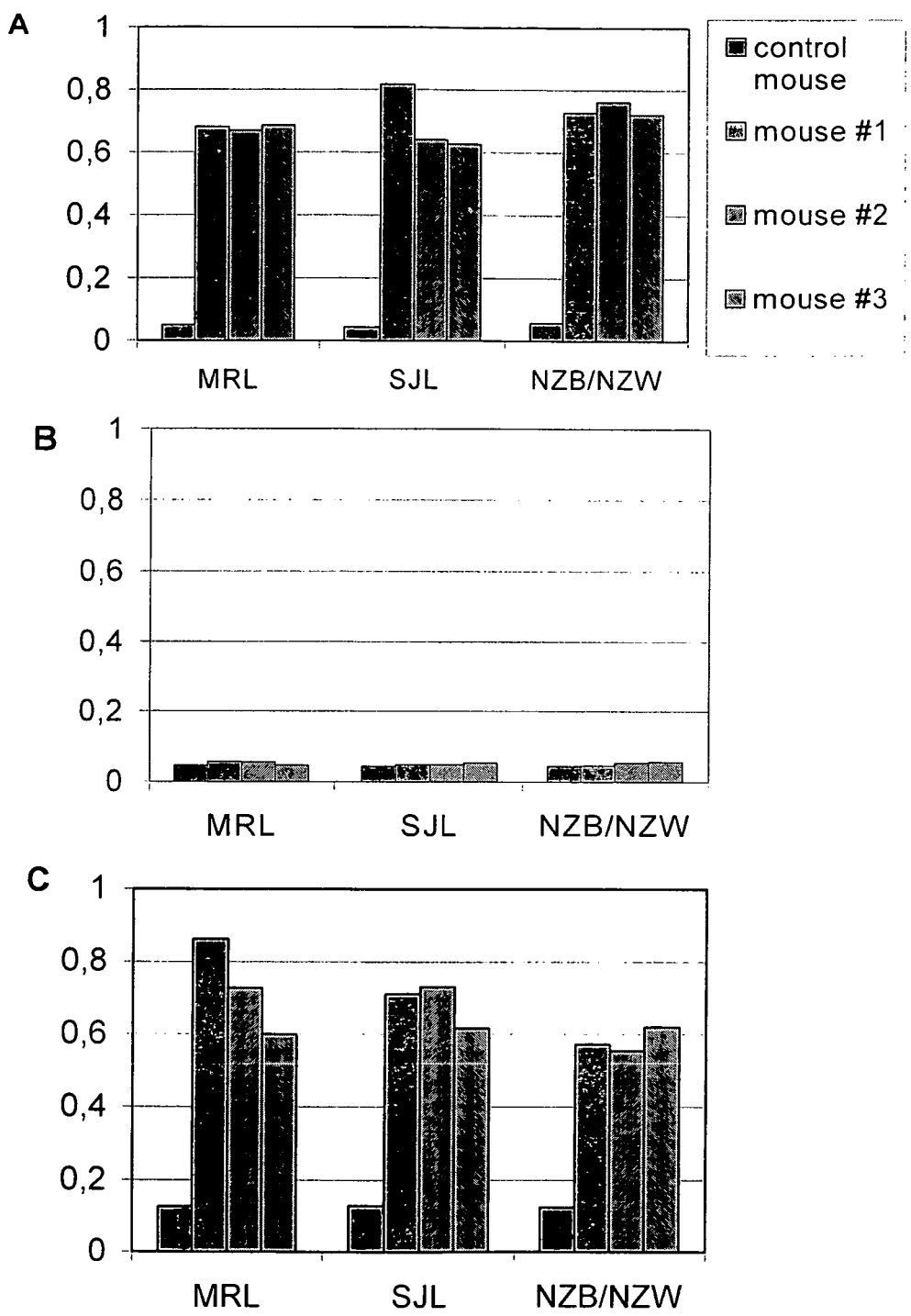

FIG. 12. Enzyme immunoassay of blood sera of SJL, MRL-lpr/lpr and NZB/NZW F1 mice immunized with peptidylphosphonate. The antigen used was: A—biotinylated reactive peptide; B—biotinylated diphenylvalylphosphonate; C—methyl p-nitrophenyl biotinylphenylmethylphosphonate.

Figure 13:
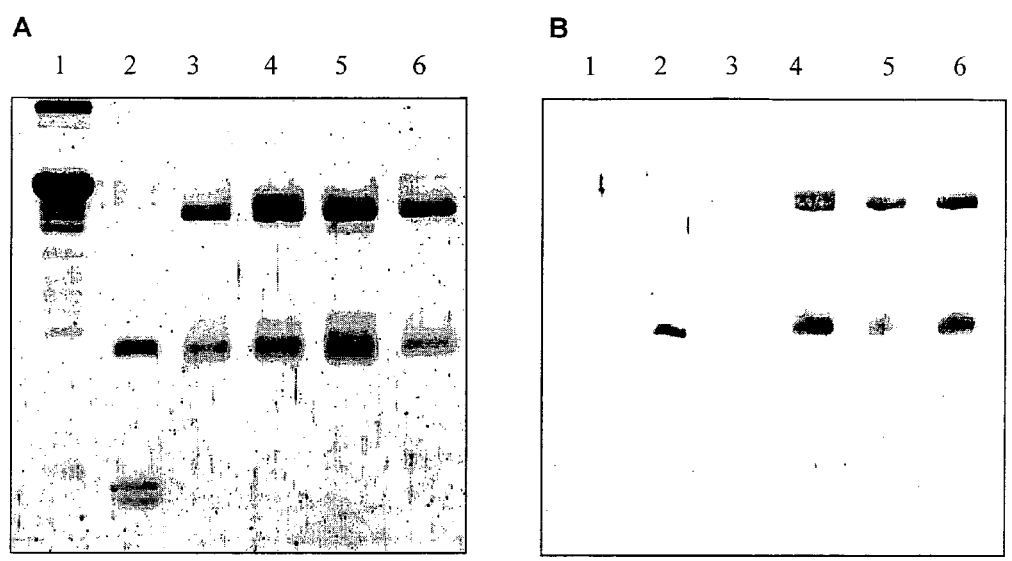

FIG. 13. Electrophoregram (A) and immunoblot (B) of polyclonal antibodies isolated from immunized mice of strains SJL (4), MRL-lpr/lpr (5) and NZB/NZW F1 (6) and covalently modified with an antigen. Lanes 1-3: 10 μg of BSA, 1 μg of trypsin, and 1 μg of IgG of BALB/c mice.

FIG. 14.

The positive test was considered if the signal for sample of all mice in the corresponding group was more than three times the background. Five animals per group were tested.

THE PREFERRED EMBODIMENTS OF THE INVENTION

The present invention is illustrated by the following Examples:

Example 1

Development of a Genetic Construct Containing a Nucleotide Sequence Encoding the Fusion Protein gp120I-IIImbp for its Expression in a Prokaryotic System 1) To induce autoimmune encephalomyelitis (EAE) in SJL mice, the 89-104 peptide of the myelin basic protein (MBP) was chosen, the peptide having the following structure: VVHFFKNIVTPRTPPPS (SEQ ID NO: 6) [Sakai, K., Zamvil, S. S., Mitchell, D. J., Lim, M., Rothbard, J. B., and Steinman, L. 1988. Characterization of a major encephalitogenic T cell epitope in SJL/J mice with synthetic oligopeptides of myelin basic protein. *J. Neuroimmunol.* 19:21-32., || Tan, L. J., Kennedy, M. K., and Miller, S. D. 1992. Regulation of the effector stages of experimental autoimmune encephalomyelitis via neuroantigen-specific tolerance induction. II. Fine specificity of effector T cell inhibition. *J. Immunol.* 148:2748-2755.] and is designated hereinafter also as peptide MBP$_{89-104}$, or as "MBP protein 89-104". The DNA sequence corresponding to said peptide was synthesized by PCR from two overlapping oligonucleotides additionally containing a stop codon and restriction sites. The resulting DNA fragment was cloned in the pET32b plasmid using NotI and XhoI restrictases. The resulting plasmid is hereinafter designated as pET32 mbp. For the accurate identification of recombinant proteins at all stages of their expression, isolation and purification, pET32bCH and pET32CHmbp constructs were engineered to contain a sequence that codes for the 10 amino acid-long fragment of immunodominant epitope of human p62 c-myc protein [Evan G. I., Lewis G. K., Ramsay G., Bishop J. M., || *Mol. Cell. Biol.* 1985, V.5(12), P. 3610-3616.], namely amino acid sequence EQKLISEEDL (SEQ ID NO: 9).

2) Numerous available publications on the structure, immunogenicity and functional activity of the surface protein gp120 [Hansen, J. E., Lund, O., Nielsen, J. O., Brunak, S., and Hansen, J.-E., S. 1996. Prediction of the secondary structure of HIV-1 gp120. Proteins. 25: 1-11|| Shioda, T., Oka, S., Xin, X., Liu, H., Harukuni, R., Kurotani, A., Fukushima, M., Hasan, M. K., Shiino, T., Takebe, Y., Iwamoto, A. and Nagai, Y. 1997. In vivo sequence variability of human immunodeficiency virus type 1 envelope gp120: association of V2 extension with slow disease progression. *J. Virol.* 71: 4871-4881 || Sullivan, N., Sun, Y., Sattentau, Q., Thali, M., Wu, D., Denisova, G., Gershoni, J., Robinson, J., Moore, J., and Sodroski, J. 1998. CD4-Induced Conformational Changes in the Human Immunodeficiency Virus Type 1 gp120 Glycoprotein: Consequences for Virus Entry and Neutralization. *J. Virol.* 72: 4694-4703] allowed allocation of protein regions having a relatively constant sequence and most promising with regard to immunization. For further work, a chimeric polypeptide was chosen, which consisted of three fragments of gp120 (designated as I, II and III) lacking the first, second and third hypervariable regions. This chimeric polypeptide (as well as the respective amino acid sequence) is designated hereinafter also as "fragment gp120 I-III". HXB2-env gene sequence was used as the initial template for the synthesis of this construct [Page, K. A., Landau, N. R., and Littman, D. R. 1990. Construction and use of a human immunodeficiency virus vector for analysis of virus infectivity. *J. Virol.* 64: 5270-5276]. Fragments I, II and III were obtained by PCR using synthetic oligonucleotides followed by assemblage of the fragments using the <<splicing by overlap extension>> approach (FIG. 1). The final PCR product I-III (designated hereinafter as "gene of gp120 I-III") and intermediate products I-II, II-III and III were cloned into the BlueScript plasmid, with subsequent recloning into the plasmids pET32b (FIG. 2: No. 8, 9, 10 and 12), pET32 mbp (FIG. 2: No. 5), pET32bCH (FIG. 2: No. 6 and 11) and pET32CHmbp (FIG. 2: No. 7) using respective restrictases, i.e., NcoI-BamHI for I-III, NcoI-NotI for I-II, EcoRV.-BamHI for II-III, and EcoRV\DraI.-BamHI for III. The products of these constructs were used to test the proteolytic activity of the antibodies against gp120 that had been obtained as a result of immunization.

The term "catalytic antibody" means an antibody that causes acceleration of particular chemical reaction (e.g. hydrolysis of peptide bond). Catalytic antibodies are also called "abzymes". Proteolityc antibody has the ability to enzymatically cleave the substrate (antigen). In the specification the terms "catalytic" and "proteolytic" are equivalent.

For immunization of SJL mice, in order to obtain proteolytic (catalytic) antibodies against gp120 glycoprotein, the final construct based on pET28a vector was engineered (FIG.

3: No. 15). The fragment NcoI-XhoI from the construct 7 were recloned into pET28a at the respective restriction sites.

For immune response testing and antigenicity assay, additional constructs basing on pET28a vector (FIG. 3: No 13, No 14, No 15, No 16) including the constructs comprising the gene of gp120I-III but no sequences encoding mbp peptide and the epitope of c-myc concurrently was obtained in a similar way as well as the protein product corresponding of these construct. Also the protein product of final construct (Construct No. 15) i.e. gp120 mbp and these additional proteins were tested for ability to induce classical antibodies against gp120 in conventional laboratory animals.

A DNA "coding sequence" or a "sequence encoding" a particular protein or peptide, is a DNA sequence which is transcribed and translated into a polypeptide in vitro or in vivo when placed under the control of appropriate regulator elements. The boundaries of the coding sequence are determined by a start codon at the 5'-terminus and a translation stop codon at the 3'-terminus. A coding sequence can include, but is not limited to, prokaryotic sequences, cDNA from eukaryoticm RNA, genomic DNA sequences from eukaryotic (e.g., mammalian) DNA, and even synthetic DNA sequences. A transcription termination sequence will usually be located 3' to the coding sequence.

As used herein the terms "fusion protein" and "fusion peptide" are used interchangeably and encompass "chimeric proteins and/or chimeric peptides" and fusion "intein proteins/peptides". A fusion protein comprises at least fragment gp120 I-III of the present invention joined via a peptide bond to at least a portion of another protein. For example, fusion proteins can comprise a marker protein or peptide, or a protein or peptide that aids in the isolation and/or purification and/or antigenicity and/or immunogenicity of a fragment gp120 I-III of the present invention The constructs basing on pET28a allow to obtain the protein product with the vector-encoded N-terminal amino acid sequence MA. Using different cloning vectors, the inventors also obtained analogous series of chimeric protein products where the initial MA dipeptide was deleted or replaced:

by another dipeptides as KK RR, RK, ED, EN, DD, AS, AT, AA, TT, SS, NN or by one or another prokaryotic leader peptide which widely used in recombinant proteomics (for example, Choi J. H, Lee S Y., Secretory and extracellular production of recombinant proteins using *Escherichia coli*. Applied Microbiology and Biotechnology, 2004, June, vol. 64, (N5), pp 625-35). including, for example, protein III of bacteriophages fd, f1, m13 (i.e. MKKLLFAIPLVVPFYSHS) (SEQ ID NO: 2) or;

by one or another of eukaryotic leader peptides which widely used in recombinant proteomics (Ladunga I. Large-scale predictions of secretory proteins from mammalian genomic and EST sequences Current Opinion in Biotechnology, 2000, February, vol. 11(N1), pp 13-8) including, for example, eukaryotic leader peptide of IgG H (heavy) chain (MNFGLRLIFLVLTLKGVQC) (SEQ ID NO: 3).

Subsequent immunizations of animals made with the said proteins modified with respect to the initial construct contained the MA dipeptide indicated that the said modifications had no significant influence on the ability of the chimeric protein to elicit specific (including, correspondingly, proteolytic) humoral immune response against full-length gp120 and gp120 fragment(s) including fragment gp120 I-III or chimeric proteins including proteins comprising gp120 fragment(s) including fragment gp120 I-III.

3) The preparation of electrocompetent cells, transformation, restrictase treatment, ligation, PCR, and DNA electrophoresis were carried out according to standard methods [Sambrook J., Fritsch E. F., Maniatis T. || Molecular Cloning: A Laboratory Manual. New York, Cold Spring Harbor Laboratory Press, 1989.].

Example 2

Expression, Isolation and Purification of the Fusion Protein gp120I-IIImbp

The fusion protein was expressed in T7-lysogenated *E. coli* cells (the strain BL21(DE3) was used in the present example). The protein was expressed as follows:

1. Competent cells are transformed with 0.1 μg of plasmid according to Item 3 of Example 1 by electroporation and seeded onto a Petri dish containing 30 μg/ml Kanamycin and 2% glucose. Bacterial colonies are grown for 12-14 h at 30° C.

2. The colonies are completely suspended in 1 l of bacterial medium 2xYT containing 30 mg/ml Kanamycin and 0.1% glucose.

3. The cell culture is grown at 30° C. under adequate aeration up to the density of 0.6-1 OU but not longer than three hours; then IPTG is added to make 1 mM and induction is carried out for 3 h at 30° C.

Fusion Protein Isolation and Purification

The fusion protein gp120I-IIImbp was isolated under denaturating conditions as follows:

1. The cell culture is centrifuged at room temperature for 10 min at 5000 rpm; the sediment is suspended in 1/50 of the initial volume in 50 mM Tris-HCl, pH 8.0; lysozyme and Triton-X100 are added to make 0.1 mg/ml and 0.1%, respectively; and the mixture is incubated for 30 min at 30° C.

2. The lysate is cooled to 0° C., sonicated up to the disappearance of viscosity, and centrifuged for 40 min at 20000 rpm.

3. The sediment is carefully suspended in 1/200 of the initial volume in a buffer containing 50 mM Tris-HCl (pH 8.0), 1 mM EDTA-Na, and 1% Nonidet P-40, centrifuged for 40 min at 20000 rpm, resuspended in chromatographic Buffer A and centrifuged under the same conditions.

4. The sediment is suspended in chromatographic Buffer A (50 mM $NaH_2PO_4$—$Na_2HPO_4$, 300 mM NaCl, and 6M urea, pH 8.0), incubated on ice for 1 h, and centrifuged for 10 min at 20000 rpm.

5. The supernatant is applied to a metal chelate column equilibrated with Buffer A at the rate of 10 column volumes per hour, and the column is washed with Buffer B (50 mM $NaH_2PO_4$—$Na_2HPO_4$, 300 mM NaCl, and 6 M urea, pH 7.0) at the rate of 30 column volumes per hour up to the discontinuation of baseline migration.

6. Elution is carried out with Buffer B (50 mM $NaH_2PO_4$—$Na_2HPO_4$, 20 mM MES—NaOH, 300 mM NaCl, and 6 M urea, pH 5.0) at the rate of 30 column volumes per hour, after which the column is equilibrated with Buffer A for the second time, and immobilized metal ions and retained proteins are removed with Buffer A containing 100 mM EDTA, pH 8.0.

7. The eluate fractions are analyzed by gel electrophoresis and combined, and proteins are precipitated by dialysis against deionized water at room temperature.

8. The protein precipitate is separated by centrifugation at 4000 rpm for 10 min, washed with 70% ethanol, suspended in a minimal volume of 70% ethanol, sonicated up to the discontinuation of particle sedimentation, and stored as suspension at +4° C. in sterile polypropylene tubes.

Fusion Protein Analysis

To confirm the identity and purity of the resulting preparations of the fusion protein gp120I-IIImbp, the following characteristics of the protein were determined:

1. The electrophoretic purity of the protein was determined by Method 1 and was found to be 97%.

2. The immunoreactivity with antibodies against c-myc epitope was determined by Method 2, and the protein was found to be immunoreactive.

3. The molecular weight (Da) by mass spectrometry was determined by Method 3 and was found to be 42307 Da, the calculated value being 42075 at the tolerated error of ±2.5%.

4. The specific sorption of the protein (%) by metal chelate sorbent was determined by Method 4 and was found to be >95%.

Analytical Methods:

1. Electrophoregram Densitometry.

Figure 4:
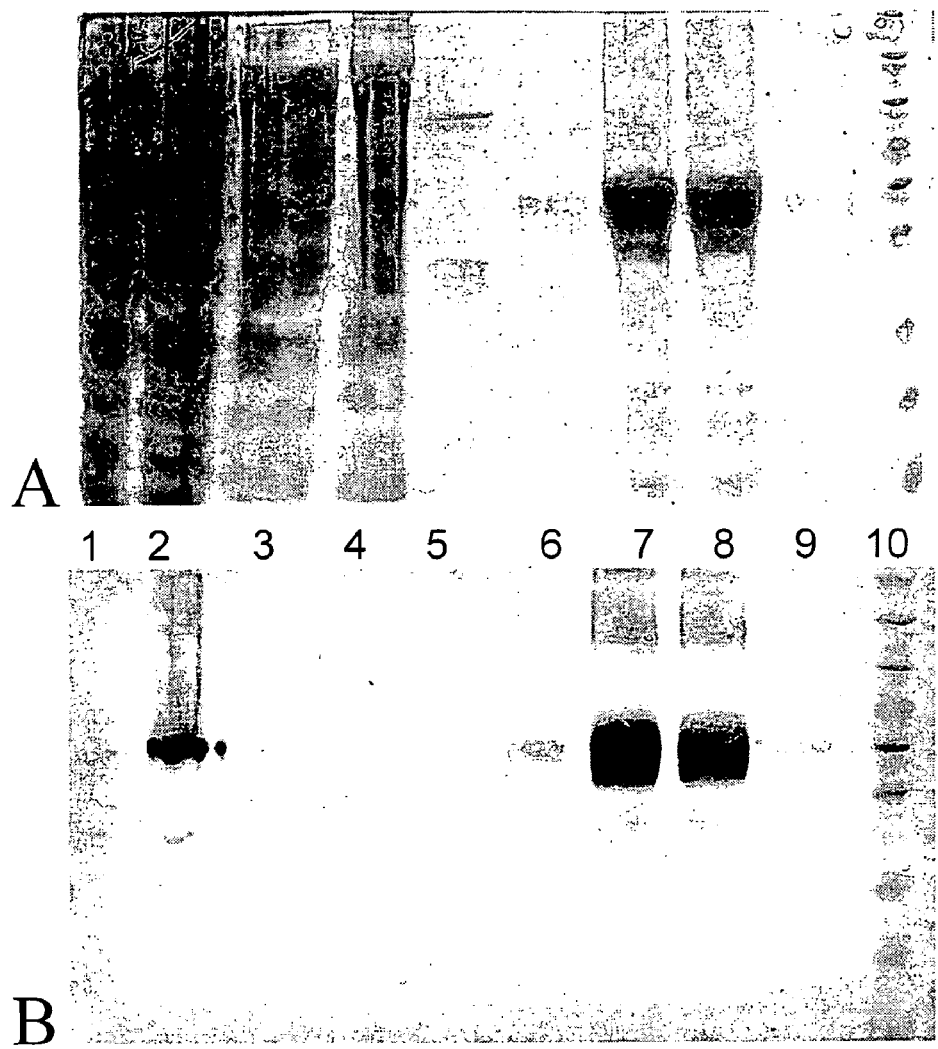
Figure 5:
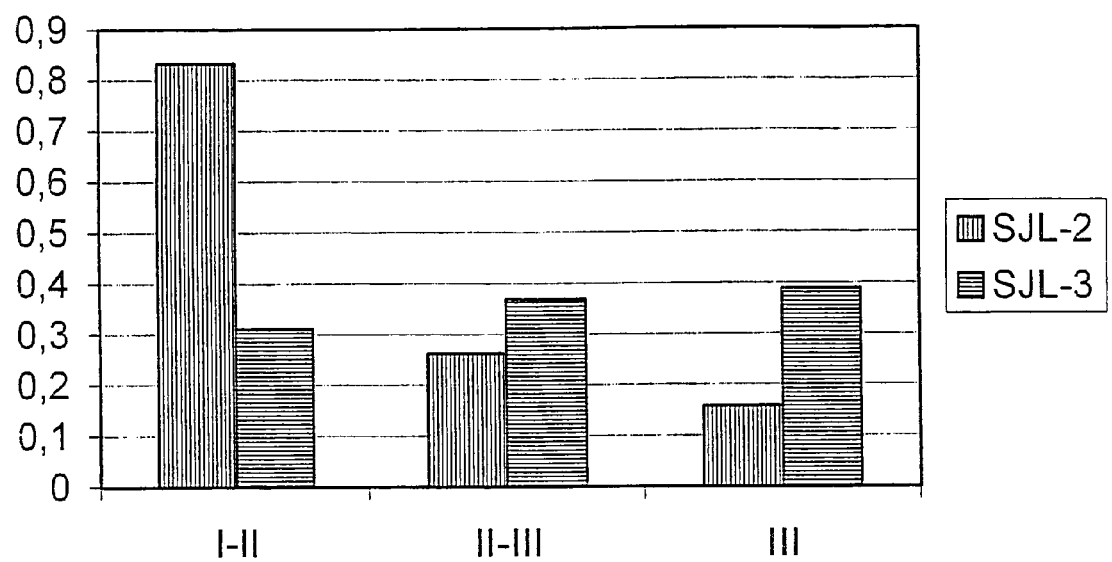

Denaturing electrophoresis of proteins was carried out according to Laemmli using 6 M urea solution in the concentrating and fractionating gels. Gel staining was carried out with Coomassie blue R-250 using contrast enhancing with a cuprum salt. Densitometry was performed with a densitometer or computer assisted plate scanner, with subsequent electrophoregram digitalization and analysis (FIG. 4A).

1. Two-component gel is prepared to have the following composition:
    Upper gel: 6.66% of acrylamide/bis-acrylamide at a 29/1 ratio, 0.1% sodium dodecyl sulphate, 0.125 M Tris-HCl, and 6 M urea, pH 6.8.
    Lower gel: 10% of acrylamide/bis-acrylamide at a 29/1 ratio, 0.1% sodium dodecyl sulphate, 0.375 M Tris-HCl, and 6 M urea, pH 8.9.

2. Protein samples are mixed with sample buffer containing 5% 2-mecaptoethanol, heated for 5 min at 100° C. and applied to gels. Electrophoresis is carried out at 25 mA until indicator dye is eluted.

3. The fractionating gel is separated and incubated for 5 min in a hot mixture of 10% ethanol and 10% acetic acid.

4. Staining is performed by gel incubation for 10 min in a hot mixture of the following composition: 15% ethanol, 25% acetic acid, 0.3 g/l Coomassie Blue R-250, and 0.45 g/l cuprum sulphate hexahydrate.

5. After staining, the gel is subjected to multiple washings, as described in Item 3, up to complete decoloration.

6. The gel is subjected to densitometry according to the densitometer specifications. Upon electrophoregram digitization with a computer-assisted plate scanner, the Green channel of color image or green light filter of the scanner is used. The electrophoregram image is analyzed using Scion Image software by Surface Plot method. The preparation purity is defined as the ratio of the main peak to the sum of all the detected peaks.

2. Immunoblotting.

Immunoblotting is carried out according to the standard regimen using blocking bovine serum albumin (BSA) solution. The hybridization buffer is supplemented with BSA (fraction V, Sigma) to make 0.5% of the final BSA concentration (FIG. 4B).

1. Electrophoresis is carried out according to Method 2 using a prestaining marker.

2. The fractionating gel is separated, whereupon the procedure of transference to HyBond N+ membrane (Amersham) is performed using an LKB apparatus for semidry electrotransference according to the manufacturer's specifications for 40 min at 0.8 mA/cm$^2$.

3. The membrane is blocked for 1 h with the solution of 50 mM Tris-HCl (pH 7.6), 150 mM NaCl and 5% bovine serum albumin (fraction V).

4. The membrane is washed thrice for 5 min with a deblocking solution containing 50 mM Tris-HCl (pH 7.6), 150 mM NaCl and 0.05% Tween-20. Then hybridization with the monoclonal antibody 1-9E10.2 is performed for 1 h in the solution of 50 Tris-HCl (pH 7.6), 150 mM NaCl and 0.5% bovine serum albumin.

5. Deblocking (washing) according to Item 4 is performed, and the membrane is hybridized with secondary rabbit Fc-specific anti-mouse IgG antibodies conjugated to horse radish peroxidase (Sigma Immunochemicals) under the same conditions as described in Item 4.

6. The membrane is deblocked as described in Item 4 and stained with the solution of 50 mM Tris-HCl (pH 7.6), 3 mg/ml 1-chloro-4-naphthol and 0.003% $H_2O_2$ for 30 min.

All the analyses are performed using primary and secondary antibody titers of 1:10000 and 1:4000, respectively, as determined with a characterized antigen, and a test protein is applied to electrophoresis at the dose of 0.1 µg. The presence of a possible test protein immunoreactivity is determined visually by the following criteria: the development of a single distinct well outlined staining zone whose electrophoretic mobility corresponds to that of the test protein. When these criteria are met, instrumental analysis is performed.

For the final semiquantitative analysis, the densitometric evaluation of the intensity of the staining zone is performed by the Surface Plot method using Scion Image software. Test results are considered positive when the peak half-height is 5 times greater than the range of baseline fluctuations on the densitogram.

3. MALDI Mass-Spectrometry.

Samples are prepared for analysis as follows.

1. An aliquot of protein suspension of a minimal volume is evaporated to dryness in a vacuum centrifuge.

2. The residue is dissolved in 1-5 µl of mixture of 1% aqueous trifluoroacetic acid and 30% acetonitrile, applied to the base plate using 2,5-dihydroxybenzoic (DHB) acid as a matrix, and analyzed.

3. A TOF MALDI mass-spectrometer, similar in performance to the VISION 2000 apparatus, is precalibrated by protein reference standards (trypsin and angiotensin), and protein mass-spectra are read using internal calibration. The masses of molecular ions are determined using VISION 2000 Mass Analyzer software taking account of the performed calibrations.

4. Specific Adsorption.

To confirm the functional properties of a protein preparation, it is tested qualitatively for adsorption from solution by excess metal chelate sorbent. Tested proteins having the sequence 6×His will be immobilized by the metal chelate sorbent at pH 8.0.

1. The required volume of the metal chelate sorbent Talon (Clontech Laboratories Inc.) is equilibrated with a buffer solution (50 mM $Na_2HPO_4$—$NaH_2PO_4$, 300 mM NaCl, and 0.1% Triton X-100) and 20 µl portions of the 1:1 suspension are transferred to test tubes.

2. 10 µg of test protein solution is added, and the volume is adjusted to 100 µl with the buffer according to Item 1. The test tubes are incubated at shaking for 15 min and allowed to stand, after which 10 µl aliquots are taken for analysis.

3. Adsorption is considered to be complete if the measured protein concentration in the test sample does not exceed 0.005

μg/ml (i.e., is not significantly different from the control when the protein concentration is determined by the BSA test), which corresponds to the 95% absorption level.

Example 3A

Immunization of Autoimmune SJL Mice with the Fusion Protein gp120I-IIImbp

SJL mice are immunized with the fusion protein gp120 I-IIImbp as follows.

1. Five female SJL mice aged 6-8 weeks are immunized twice at a weekly interval with the antigen in complete Freund adjuvant having the final *M. tuberculosis* concentration of 2 mg/ml and the antigen concentrations of 1.5 mg/ml and 3 mg/ml.

2. Injections at the total volume amounting to 0.1 ml of the preparation are done subcutaneously at three sites along the back in case of the first immunization, and into paw pads, in case of the second immunization.

3. To compromise the hematoencephalic barrier, one day before the first immunization and two days after it the mice are additionally intraperitoneally injected with 400 ng of pertussis toxin preparation.

4. Seventeen days after the first immunization, the mice receive a boosting peritoneal injection of the antigen in PBS at the total volume amounting to 0.2 ml, the dose of the immunogenic protein being 50 μg per mouse.

5. Concurrently with the boosting procedure, blood is taken from the orbital sinus of experimental and control (non-immunized) mice to monitor the development of the immune response. The presence of specific antibodies in the blood serum is determined by enzyme immunoassay.

6. Twenty one days after the beginning of the experiment, the mice that have showed the maximal antigen-specific response in immunochemical testing are used for splenectomy and blood sampling. The spleens are used for cell fusion in order to obtain hybridoma clones and for mRNA isolation for the subsequent cloning as phage display libraries.

Example 3B

Immunization of Conventional Mice (BALB/c) with the Products of Different Chimeric Proteins (the Protein Products of Constructs No. 13-16 (See FIG. 3)

The products of Constructs Nos. 13-16 (see FIG. 3) were used as antigens for immunization (immunogens). The control mice were treated with phisiological solution. Twenty one days after the immunization all mice are used for splenectomy and blood sampling. The BALB/c mice were immunized in the same manner as described in Example 3A with the exception of step 3. Control mice were treated by complete Freund adjuvant having the final *M. tuberculosis* concentration of 2 mg/ml and the antigen concentrations of 1.5 mg/ml and 3 mg/ml. The all mice are used for blood sampling for estimation of immunologic response.

Example 3C

Estimate of the Antigen-Specific Antibodies

To estimate the appearance of:

antigen-specific proteolytic antibodies (from SGL mice) in the course of immunization performed against the background of induced autoimmune pathology manifested as preclinical experimental autoimmune encephalomyelitis, antigen-specific antibodies (from Balb/c mice) in the course of immunization performed against gp120 fragments-containing proteins the following tests are carried out:

Analysis of the Antigen Specificity and Proteolytic Activity of the Obtained Polyclonal Antibody Preparations.

1. Analysis of the Antigen Specificity of Polyclonal Antibody Preparations Obtained as from the Conventional (Balb/c) as from Autoimmune SJL Mice.

For the initial comparative monitoring of the specific immune response to the antigen in immunized mice, enzyme immunoassay (EIA) is used (FIG. 5).

An antigen is immobilized on an immunological plate and, after incubation with sera obtained from immunized and control mice, antigen-antibody complex is detected with Fc-specific rabbit antimouse-IgG antibodies conjugated to horse radish peroxidase. The sera of immunized and control mice are used at several dilutions (1:12 and 1:48). The following recombinant proteins are used as antigens:

1) trx-gp120 I-III-CH, a fusion protein comprising *E. coli* thioredoxin A, a gp120 sequence lacking the first, second and third variable regions, and $His_6$-c-myc sequence ($His_6$ disclosed as SEQ ID NO: 22); it is corresponding to product of Construct No. 6 (see FIG. 2).

2) trx-gp120 I-II-H, a fusion protein comprising *E. coli* thioredoxin A, the sequences of the first and second constant regions of gp120, and $His_6$ sequence (SEQ ID NO: 22); it is corresponding to product of Construct No. 9 (see FIG. 2).

3) trx-gp120 I-III-H, a fusion protein comprising *E. coli* thioredoxin A, the sequence of the second constant regions of gp120, with the C-terminus of the sequence starting from the third constant region, and $His_6$ sequence (SEQ ID NO: 22); it is corresponding to product of Construct No. 12 (see FIG. 2).

4) trx-gp120 III-H, a fusion protein comprising *E. coli* thioredoxin A, the C-terminus of the gp120 sequence starting from the third constant region, and $His_6$ sequence (SEQ ID NO: 22); it is corresponding to product of Construct No. 10 (see FIG. 2).

5) trx-CH, a fusion protein comprising *E. coli* thioredoxin A and $His_6$ sequence (SEQ ID NO: 22), which was used as the negative control to determine the non-specific binding of obtained antibodies to these protein sequences; it is corresponding to product of Construct No. 6 (see FIG. 2).

6) Full length HIV-1 recombinant gp120 glycoprotein.

As a result of the performed experiments (FIG. 5), it has been shown that all the antibody preparations obtained from the blood serum of mice immunized with a fusion protein interact with the antigens. It has been observed as for conventional (BALB/c) mice and for autoimmune (SJL mice). The immunogenic potential of different chimeric proteins are presented in FIG. 14. The antibody against recombinant gp120 or chimeric protein containing I, II or III fragment of gp120 or containing its combination (I and III), (I and II), (II and III) or (I, II, III) was developed after immunization both autoimmune and normal mice by a chimeric protein having gp120 I-III amino acid chain (fragment gp120 I-III) in its structure. The additional experiments conducted with other (similar) chimeric proteins having fragment gp120 I-III in its structure and optionally the short amino acid "tail" (up to 50-60 amino acids), have shown the similar results.

2. Analysis of the Proteolytic Activity of Polyclonal Antibody Preparations Antibody Preparations Obtained from Autoimmune SJL Mice.

Figure 6:
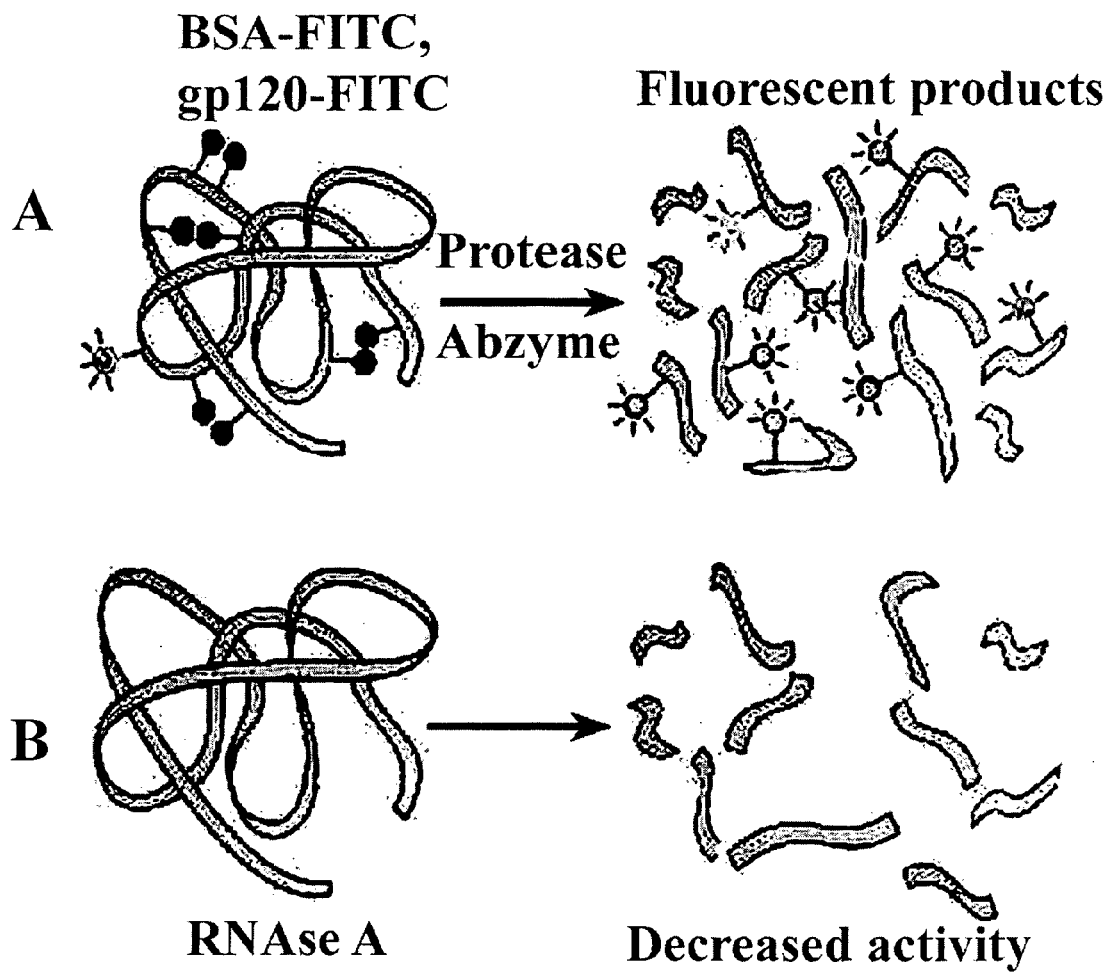

To determine the proteolytic activity, the antibodies are, as a preliminary, purified by affinity chromatography using recombinant protein G immobilized on Sepharose. The activity is detected by two different methods (FIG. 6).

A. Fluorescent assay. The principle of the method, which is outlined in FIG. 6A, is based on the phenomenon of fluorescence quenching by a protein heavily labeled with a fluorophore, which phenomenon is described in literature and is mainly based on the mutual interactions of the aromatic rings of different fluorophore molecules (e.g., because of intense hydrophobic and stacking contacts), and on fluorescence enhancement by introduction of breaks into the polypeptide chain. In the present test, bovine serum albumin and the recombinant protein trx-gp120 I-III-CH excessively labeled with fluorescein isothiocyanate (designated hereinafter as BSA-FITC and gp120-FITC) were used as the substrates for the proteolysis. The reaction was monitored by the fluorescence enhancement vs. control. Trypsin devoid of contaminating chymotrypsin activity was used as the model protease to determine the sensitivity of the method and to evaluate temporal signal changes depending on the substrate and enzyme amounts.

Figure 8:
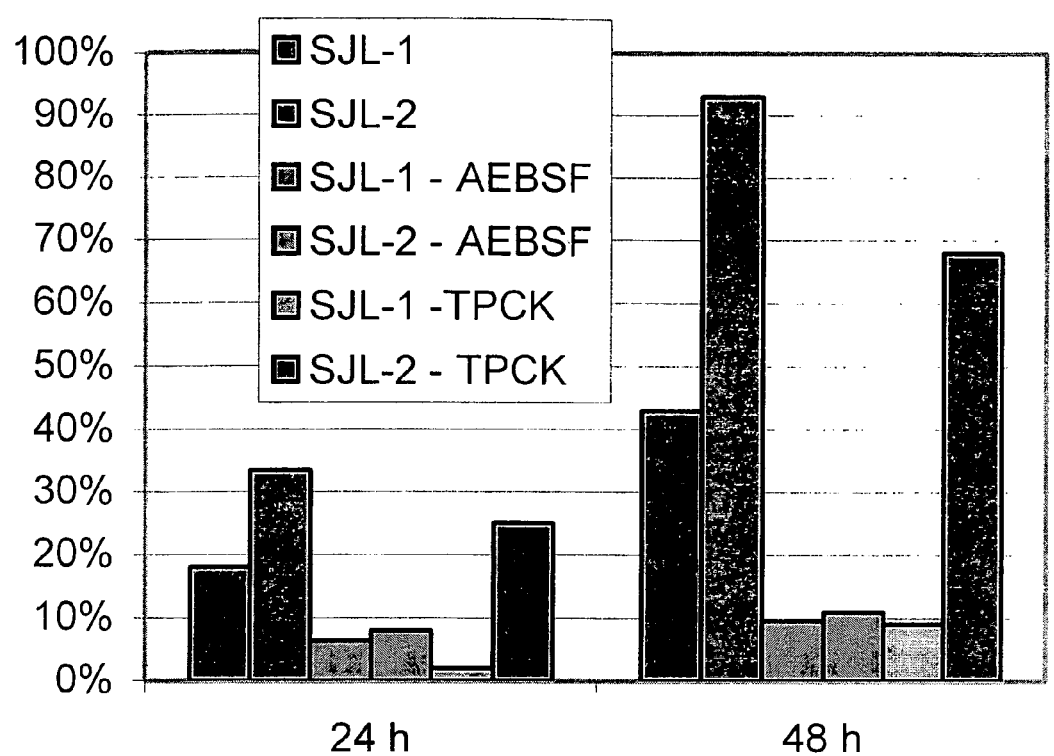

To determine the proteolytic activity of the tested antibody preparations, triplicate measurements are carried out at the baseline and after incubation at 37° C. for 24 h and 48 h. The results of these experiments suggest the following (FIGS. 7-9):

First, the proteolytic activity of preparations obtained from mice immunized with the protein gp120 I-IIImbp is increased in comparison with control SJL mice when both substrates are used.

Second, the increase in the antigen-specific proteolytic activity is predominantly responsible for the total increase. With gp120-FITC, the signal increased from ten to twenty times in comparison with non-immunized mice, whereas with BSA-FITC, the signal increased twofold only.

Third, the predominant mechanism is, in this case, the serine-dependent catalysis, because the addition of serine-reactive irreversible inhibitors resulted in a significant reduction in the observed rate of hydrolysis of BSA-FITC.

Forth, IgG molecules, which are selectively removed from the reaction by immunoprecipitation, are responsible for, at least, a major part of the observed proteolytic activity.

Along with undisputed advantages, such as high sensitivity and the simplicity and rapidity of measurements, this method, unfortunately, has some drawbacks, the main of which is complex nonlinear relationships between fluorescence changes and substrate and enzyme amounts, sample volume, buffer composition and pH, etc. resulting in difficulties in the quantitative evaluation and characterization of the enzymatic activity of polyclonal antibody preparations. Besides that, proteolytic activity determination by this test requires a large excess of substrate vs. enzyme, because the real amount of abzymes in the total pool of antibodies may make a few percents or less.

With regard to the above, another method for determination of the proteolytic activity of the obtained antibody preparations was used as an alternative.

B. Enzymatic Assay.

The principle of this method of detection of proteolytic activity, which is outlined in FIG. 6B, is based on the use of small amounts (about 1 ng per reaction) of a highly active enzyme ribonuclease A as the substrate of the proteolysis reaction. The level of ribonuclease activity, which linearly depends on the concentration of active RNAase A, is determined by the acid-soluble residue method using polycytidyl acid as the polymeric substrate of the reaction. This method of proteolytic activity detection presumably allows achieving a significant molar excess of enzyme vs. substrate and thus makes the conditions of the proteolysis reaction under study closer to those of the well-studied non-stationary kinetics model ($[S]_0 << [E]$).

To eliminate possible artefacts, all the antibody preparations under study were tested for the intrinsic ribonuclease activity and the presence of solution components that nonenzymatically alter the added ribonuclease activity. All the antibody preparations under study were devoid of the intrinsic ribonuclease activity and did not alter the added ribonuclease activity upon a short-time (10 min) incubation of the reaction.

The proteolytic activity of the tested antibody preparations was measured under the following conditions: IgG concentration 0.1 mg/ml, incubation time 17 h, temperature 37° C. The preparation activity measured by this method was expressed as ribonuclease hydrolysis rate.

The test results presented in FIG. 10 show that proteolytic activity decreased 1.5-2 times upon immunization of mice with gp120-I-IIImbp. These results are in a limited correspondence with the results of the fluorescent test: only the negative correlation between the proteolytic activity and the immunogen dose used for immunization is reproduced. There is no 'obvious' logic indicating that the titer of catalytic antibodies or its specific catalytic activity must increase with the increase in the antigen concentration within the described window. Lack of straighforward logic noted above is supported by the notion that the causatives of the catalytic immune response are complex and still largely unknown. First, immunization with the encephalitogenic peptide causes primarily T-cell response and tolerance breakdown only at the appropriate genetic background. How this background influences the further antibody response, is unknown, however, under certain conditions, the antigens like MBP or MOG (myelin oligodendrocyte protein) cause tolerization rather than tolerance breakdown. It is therefore difficult to expect that the following will be natural in the discussed case 1) that the total anti-MBP autoantibody production during artificial induction of EAE will follow general rules of "classic" immune response; 2) that the proportion of catalytic antibodies will follow the same rules, i.e. will necessarily increase if the amount of the antigen increase (even though the amount of binding antibodies will indeed increase).

The discrepancy between the results of the fluorescent and enzymatic analysis might be explained by differences between the structures of the substrates of proteolysis. Presumably, RNAase A globule compared with BSA globule has fewer sites available for proteases and abzymes. Since, upon immunization, the total serum concentration of IgG increases manifold by antigen-specific antibodies, the proportion of the initial proteolytic antibodies decreases, whereas the newly-formed antigen-specific proteolytic antibodies are, most likely, inefficient catalyzers of proteolytic cleavage of RNAase A.

3. Monitoring of Immune Response Development and Experimental Autoimmune Encephalomyelitis Induction.

To characterize the features of immune response development upon immunization with a fusion protein comprising the neuroantigen MBP, a comparative analysis of specific surface markers expression in T-lymphocytes from SJL mice that were not immunized (control), from mice immunized with the synthetic peptide $MBP_{89-104}$, recombinant fusion protein gp120I-IIImbp (the product of Construct No. 15 (see FIG. 3) at two different doses and recombinant protein gp120I-III (the product of Construct No. 13 (see FIG. 3) was carried out (FIG. 11). All the immunizations were performed in parallel under identical conditions as described above. Twenty one days after the beginning of an experiment, CD4+ T-lymphocytes isolated from two mice of each group were analyzed by flow cytometry. A specific feature of SJL mice was initially low CD8+ T-cell counts. Also, changes in the expression of the following surface markers important for immune response development have been studied: CD11a, CD44, CD45RB, and CD62-L. The results presented in FIG. 11 suggest that in case of immunization with the peptide MBP and, also, with fusion proteins comprising this antigen, a fully developed T-cell immune response (memory cells appeared) was induced in mice by day 21 after the immunization, whereas in case of use of solely gp120I-III as the antigen, the immune response was still developing. The similar results were obtained in SJL mice for products of Constructs Nos 14 and 16, correspondingly).

The obtained data provide an evidence of the enhancement of immune response development when the autoantigen MBP is used and of T-lymphocyte activation typical of experimental autoimmune encephalomyelitis development.

Thus, the above Example shows that, upon immunization of SJL mice with the fusion protein gp120I-IIImbp, antigen-specific proteolytic antibodies are generated against the background of the preclinical stage of induced experimental autoimmune encephalomyelitis.

Example 4

Synthesis of Reactive Phosphonate Derivative of Peptide Fragment of gp120

At the first stage, aminoalkylphosphonates protected at their free amino group are synthesized in the reaction of co-condensation of triphenylphosphite, isobutanal, and benzylcarbamate. To this end, the mixture of triphenylphosphite, isobutanal, and benzylcarbamate, 0.1 mole each, in 15 ml of glacial acetic acid is stirred for about 1 h until heat generation discontinues. After that, the reaction is stirred with heating to 80° C. for 1 h. After the full completion of the reaction, volatile products are removed with a rotary evaporator under reduced pressure and heating on a water bath. The oily residue is dissolved in methanol (180 ml) and left for crystallization at −20° C. for 3 h. After crystallization, the residue of diphenyl 1-(N-benzyloxycarbonyl)-aminoalkylphosphonate is harvested by filtration and recrystallized in a minimal volume of chloroform (30-40 ml) followed by the addition of four volumes of methanol.

To obtain free amynoalkylphosphonate, the protective group is removed by treatment of diphenyl 1-(N-benzylcarbonyl)-aminoalkylphosphonate with a 33% solution of hydrogen bromide in acetic acid (15 ml per 0.1 mole) for 1 h at room temperature. Volatile components are removed with a rotary evaporator at a reduced pressure and heating on a water bath. 1-(N-benzyloxycarbonyl)-aminoakylphosphonate hydrobromide is crystallized from the resulting residue by addition of anhydrous diethyl ether. Free phosphonate is obtained by passing gaseous dry ammonium through phosphonate hydrobromide suspension in diethyl ether until the formation of a thick precipitate of ammonium bromide discontinues and the full blooming of the suspension is observed. The resulting ammonium bromide is removed by filtration, and diethyl ether is evaporated on a water bath under atmospheric pressure.

To obtain the hapten Leu-Ala-Glu-Glu-Glu-Val-$^P(OPh)_2$ (LAEEEV-$^P(OPh)_2$) (SEQ ID NO: 23), where $^P(OPh)_2$ means the substitution of the α-carboxylic group with diphenylphosphonate, the peptide Boc-Val-Ala-(t-Bu)Glu-(t-Bu)Glu-(t-Bu)Glu (SEQ ID NO: 24) protected at its N-terminal amino group and side groups is first synthesized. The peptide Boc-Val-Ala-(t-Bu)Glu-(t-Bu)Glu-(t-Bu)Glu (SEQ ID NO: 24) is fused with the phosphonate derivative of valine by mixing of 2 μmoles of the protected peptide, 2 μmoles of the phosphonate, and 2 μmoles of dicyclohexylcarbodiimide in 300 l of acetonitrile and incubating for 1 h. After the completion of the reaction, its products are separated by reverse phase HPLC on a 150×3.9-mm Waters C18 NovaPak column using 0% to 80% gradient of acetonitrile in 20 nM potassium phosphate (pH 7.0). The resulting fractions are analyzed by mass-spectrometry (MALDI-TOF). The fractions that contain substances with molecular ion masses of 1145 Da ($[M+H]^+$), 1167 Da ($[M+Na]^+$) or 1183 Da ($[M+K]^+$) are combined and freeze-dried. The residue is dissolved in 100 l of 100% trifluoroacetic acid and incubated for 1 h at room temperature to remove protective tert-butyloxycarbonyl and tert-butyl groups. The deblocked peptidylphosphonate is precipitated by addition of 10 volumes of anhydrous diethyl ether to the reaction. The precipitate is separated by centrifuging for 10 min at 12500 rpm, and the deblocking procedure is repeated. The residue is air-dried and stored at −20° C.

Analysis of the Peptidylphosphonate LAEEEV-$^P(OPh)_2$ (SEQ ID NO: 23)

I. MALDI-TOF Mass-Spectrometry.

1. A minimal amount of dry peptidylphosphonate, to which 5 μl of acetonitrile is added, is applied to a base plate using aqueous strong acid-free 2,5-dihytroxybenzoic (DHB) acid as the matrix, and analysis is carried out.

2. A TOF MALDI mass-spectrometer equivalent to the VISION 2000 apparatus is precalibrated with reference standards within the 500-2000 Da m/z range, and mass spectra of test samples are obtained using internal calibration. Molecular ion masses are determined using VISION 2000 Mass Analyzer software with the calibration taken into account. The expected result of the analysis is the presence of peaks corresponding to masses of 877.36, 900.34, and 915.45±1 Da.

II. Analytical Reverse Phase HPLC.

1. To a 0.2 mg sample of peptidylphosphonate, 100 μl of 20 mM potassium phosphate buffer (pH 7.0) containing 20% acetonitrile is added.

2. The resulting sample is administered into an injector, and gradient elution is carried out using a 150×3.9 mm Waters C18 NovaPak column for reverse phase HPLC under the following conditions:
  buffer A is 20% acetonitrile and 20 mM potassium phosphate, pH 7.0;
  buffer B is 80% acetonitrile and 20 mM potassium phosphate, pH 7.0;
  the elution rate is 1.0 ml/min at a linear 100% A to 100% B gradient for 20 min followed by 100% B for 10 min; and
  the chromatograms are recorded at 260 nm wavelength.

3. The peaks are integrated without correction for the baseline. The retention time of the main peak, which has the maximal area, is determined, and the ratio of the main peak area to the sum of all the peak areas is calculated. The expected result: the retention time is 14.75-15.25 min; the chromatographic purity is >95%.

III. Inhibition of the Esterolytic Activity of Chymotrypsin.

1. 0.5 ml of 1 µM solution of α-chymotrypsin in a buffer containing 0.1 HEPES and 0.5 M NaCl, pH 7.2, is prepared. The solution is divided into nine 50-µl aliquots, and the residue is discarded.

2. Eight dilutions of the test peptidylphosphonate in acetonitrile ranging from 100 µl to 1 µl are prepared.

3. To each of the first eight aliquots of the enzyme solution 5 µl of corresponding peptidylphosphonate solution are added, and 5 µl of acetonitrile are added to the ninth aliquot.

4. The samples are incubated for 1 h at 25±5° C.

5. The samples are successively transferred to a spectrophotometer cell containing 450 µl of deionized water, mixed, whereupon 10 µl of p-nitrophenylacetate solution in methanol (2.5 mg/ml) are added, after which the increase in the optical density at a 400-nm wavelength is recorded. The initial rate of the substrate hydrolysis is calculated in arbitrary units.

6. The effective inhibitor concentration is calculated. To this end, the ratios of the hydrolysis rates observed with samples 1-8 to the hydrolysis rate observed with sample 9 are calculated. The effective inhibitor concentration is determined as the lowest concentration of the test substance, at which the ratio of the rates of substrate hydrolysis does not exceed 50%. The expected result: 30 µM.

Example 5

Reactive Immunization of Mice with the Phosphonate Derivative of a Peptide Fragment of gp120

For immunization, the reactive peptide is conjugated to the macromolecular carrier C. conholepas hemocyanin (keyhole limpet hemocyanin, KLH). At the first stage, the carrier is activated with excess bis(sulfosuccinimidylyl)suberate in PBS for 1 h at 37° C. After the activation, KLH unbound to bis(sulfosuccinimidylyl)suberate is removed from the reaction by sevenfold exhaustive ultrafiltration (with the residual volume not more than 70 µl) using a Microcon 100 concentrator (Amicon YC membrane), each time adding PBS to the residue to make 500l and discarding the ultrafiltrate. To the resulting solution peptidylsulfonate solution in PBS is added whereupon the solution is incubated for 1 h at 37° C. without stirring. The unreacted succinimide groups are inactivated by addition of 2 µl of 2-ethanolamine. The low molecular components of the reaction are removed by sevenfold exhaustive ultrafiltration (with the residual volume not more than 70 µl) using a Microcon 100 concentrator (Amicon YC membrane), each time adding PBS to the residue to make 500 µl and discarding the ultrafiltrate. The final preparation is sterilized by filtration and stored at −20° C.

Female MRL-lpr/lpr, SJL and NZB/NZW $F_1$ mice aged 6-8 weeks are intraperitoneally immunized with the antigen in complete Freund adjuvant, with the total volume being 0.2 ml, at the dose of 50 µg of the immunogenic protein per mouse.

The second immunization is done with the same volume and at the same antigen concentration in incomplete Freund adjuvant in 17 days after the first immunization. Concurrently, blood is withdrawn from the orbital sinus of three mice of each experimental group and control non-immunized mice of the three strains to monitor the development of the immune response.

Twenty one days after the beginning of the experiment, the mice that showed the maximal antigen-specific response in immunological tests are sacrificed for splenectomy. Polyclonal antibodies isolated from the blood serum of these mice are analyzed for antigen specificity and catalytic activity.

A part of the peptidylphosphonate synthesized at the previous stages is used in the reaction of conjugation to N-hydroxysuccinimide ester of biotin. The reaction is conducted by mixing of equimolar amounts of peptidyl sulfonate and activated biotin in a minimal volume of dimethylformamide and incubation for 1 h. The biotinylated preparations are intended for analysis of the specificity of the antibodies obtained as a result of reactive immunization of mice.

To monitor the specific immune response to the antigen in several immunized mice of all the three strains, enzyme immunoassay is used.

Antibodies from the blood sera of immunized and control mice are isolated with plate-preabsorbed goat antibodies against murine IgG, with subsequent incubation with the biotinylated antigen and detection of antigen-antibody complexes using neutravidin conjugated to horse radish peroxidase. The blood sera of immunized and control mice are used at several dilutions (1:12 and 1:48). The antigens employed are biotin-labeled starting peptidylphosphonate, biotinylated Val-phosphonate, and nitrophenylmethyl-p-biotinylphenylmethylphosphonate, for which the specific covalent modification of the active center of abzymes was demonstrated earlier. The comparative analysis has shown (FIG. 12) that the antibodies of the experimental mice of all the three strains, on the whole, possess a high specificity toward the modified peptide fragment of an antigen, do not interact under the conditions of the present experiment with free Val-phosphonate, and exhibit the ability to covalently bind to a more active and less specific modifying agent. It should be noted that, on the average, in New Zealand hybrids the amount of antigen-specific antibodies was somewhat higher in comparison with the two other autoimmune strains, whereas the antibodies of MRL-lpr/lpr mice where more effective with regard to covalent modification.

Along with an antigen, horse radish peroxidase-conjugated rabbit antibodies against the Fc fragment of murine IgG are used to determine the total amount of murine antibodies specifically absorbed in a plate well. This allows estimation of the proportion of antigen-specific antibodies in the total pool of class G immunoglobulins.

Further studies of the type of interaction of the obtained antibodies with a reactive peptide were carried out with pre-purified IgG preparations using immunoblotting. After incubation with biotinylated peptidylphosphonate, electrophoretic fractionation under denaturing and reducing conditions, and membrane immobilization, antigen-antibody complexes were detected using neutravidin conjugated to horse radish peroxidase. The results of this experiment presented in FIG. 13 suggest that both light and heavy immunoglobulin chains capable of being covalently modified by the peptide were present in the preparations of polyclonal antibodies isolated from autoimmune mice immunized with the reactive peptide Val-Ala-Glu-Glu-Glu-Val-PO(OPh)$_2$ (SEQ ID NO: 25).

Thus, the reactive immunization under the conditions of the present Example has produced the following results:
The antibodies obtained in the course of immunization bind to immunization antigen.

The antibodies do not react with the "minimal" phosphonate group of immunization antigen, which means that there is no nonspecific interaction (or nonspecific chemical reaction) between the antibodies under study and the free phosphonate group of $Val^P(OPh)_2$.

The antibodies react with the active "mechanism-dependent" phosphonate, i.e., display the ability to react with a molecule that has no apparent structural relation to immunization antigen but has the ability to form covalent complexes with hydrolases.

The antibodies form covalent complexes with immunization antigen.

In combination, the above properties suggest that in the course of immunization with a peptidylphosphonate whose composition corresponds to LAEEEV (SEQ ID NO: 23)-$^P$(OPh)$_2$ epitope-specific catalytic antibodies are generated.

INDUSTRIAL APPLICABILITY

The invention may be useful in medicinal industry for manufacturing drugs and development of method for treatment HIV infection.

We claim:

1. An isolated protein comprising the amino acid sequence of SEQ ID NO: 1:

TEKLWVTVYYGVPVWKEATTTLFCASDAKAYDTEVHNVWATHACVPTDPN

PQEVVLSCNTSVITQACPKVSFEPIPIHYCAPAGFAILKCNNKTFNGTGP

CTNVSTVQCTHGIRPVVSTQLLLNGSLAEEEVVIRSVNFTDNAKTIIVQL

NTSVEINCTHCNISPAKWNNTLKQIASKLREQFGNNKTIIFKQSSGGDPE

IVTHSFNCGGEFFYCNSTQLFNSTWFNSTWSTEGSNNTEGSDTITLPCRI

KQIINMWQKVGKAMYAPPISGQIRCSSNITGLLLTRDGGNSNNESEIFRP

GGGDMRDNWRSELYKYKVVKIEPLGVAPTKAK.

2. The protein according to claim 1, wherein said protein has the following amino acid sequence structure: $Z_1$—X—$Z_2$, wherein $Z_1$ is a sequence of from 0 to 19 amino acid residues, $Z_2$ is a sequence of from 0 to 50 amino acid residues, and if $Z_1$ or $Z_2$ is zero amino acid residues, then $Z_1$ is —H (hydrogen) and/or $Z_2$ is —OH (hydroxyl group); and X is the amino acid sequence of SEQ ID NO: 1.

3. A variant of the protein of claim 2, wherein said variant has the amino acid sequence of SEQ ID NO 11:

MATEKLWVTVYYGVPVWKEATTTLFCASDAKAYDTEVHNVWATHACVPTD
PNPQEVVLSCNTSVITQACPKVSFEPIPIHYCAPAGFAILKCNNKTFNGT
GPCTNVSTVQCTHGIRPVVSTQLLLNGSLAEEEVVIRSVNFTDNAKTIIV
QLNTSVEINCTHCNISRAKWNNTLKQIASKLREQFGNNKTIIFKQSSGGD
PEIVTHSFNCGGEFFYCNSTQLFNSTWFNSTWSTEGSNNTEGSDTITLPC
RIKQIINMWQKVGKAMYAPPISGQIRCSSNITGLLLTRDGGNSNNESEIF
RPGGGDMRNWRSELYKYKVVKIEPLGVAPTKAK.

4. A variant of the protein of claim 2, wherein said variant has the amino acid sequence of SEQ ID NO 13:

MATEKLWVTVYYGVPVWKEATTTLFCASDAKAYDTEVHNVWATHACVPTD
PNPQEVVLSCNTSVITQACPKVSFEPIPIHYCAPAGFAILKCNNKTFNGT
GPCTNVSTVQCTHGIRPVVSTQLLLNGSLAEEEVVIRSVNFTDNAKTIIV
QLNTSVEINCTHCNISRAKWNNTLKQIASKLREQFGNNKTIIFKQSSGGD
PEIVTHSFNCGGEFFYCNSTQLFNSTWFNSTWSTEGSNNTEGSDTITLPC
RIKQIINMWQKVGKAMYAPPISGQIRCSSNITGLLLTRDGGNSNNESEIF
RPGGGDMRDNWRSELYKYKVVKIEPLGVAPTKAKLDPNSSSVDKLAAALE
HHHHHH.

5. A variant of the protein of claim 2, wherein said variant the amino acid sequence of SEQ ID NO 15:

MATEKLWVTVYYGVPVWKEATTTLFCASDAKAYDTEVHNVWATHACVPTD
PNPQEVVLSCNTSVITQACPKVSFEPIPIHYCAPAGFAILKCNNKTFNGT
GPCTNVSTVQCTHGIRPVVSTQLLLNGSLAEEEVVIRSVNFTDNAKTIIV
QLNTSVEINCTHCNISRAKWNNTLKQIASKLREQFGNNKTIIFKQSSGGD
PEIVTHSFNCGGEFFYCNSTQLFNSTWFNSTWSTEGSNNTEGSDTITLPC
RIKQIINMWQKVGKAMYAPPISGQIRCSSNITGLLLTRDGGNSNNESEIF
RPGGGDMRDNWRSELYKYKVVKIEPLGVAPTKAKLDPNSSSVDKLAAAVV
HFFKNIVTPRTPPPS.

6. A variant of protein of claim 2, wherein said variant has the amino acid sequence of SEQ ID NO 17:

MATEKLWVTVYYGVPVWKEATTTLFCASDAKAYDTEVHNVWATHACVPTD
PNPQEVVLSCNTSVITQACPKVSFEPIPIHYCAPAGFAILKCNNKTFNGT
GPCTNVSTVQCTHGIRPVVSTQLLLNGSLAEEEVVIRSVNFTDNAKTIIV
QLNTSVEINCTHCNISRAKWNNTLKQIASKLREQFGNNKTIIFKQSSGGD
PEIVTHSFNCGGEFFYCNSTQLFNSTWFNSTWSTEGSNNTEGSDTITLPC
RIKQIINMWQKVGKAMYAPPISGQIRCSSNITGLLLTRDGGNSNNESEIF
RPGGGDMRDNWRSELYKYKVVKIEPLGVAPTKAKLDPHHHHHHGSGEQKL
ISEEDLNSSSVDKLAAAVVHFFKNIVTPRTPPPS.

\* \* \* \* \*